(12) United States Patent
Ito et al.

(10) Patent No.: US 7,402,732 B2
(45) Date of Patent: Jul. 22, 2008

(54) PARAQUAT RESISTANCE GENE AND A VASCULAR TISSUE—AND TRICHOME-SPECIFIC PROMOTER

(75) Inventors: Hisashi Ito, Kurashiki (JP); Yoshikazu Tanaka, Tsuruga (JP); Kenichi Ogawa, Okayama (JP); Satoshi Kondo, Aichi (JP); Chikara Ohto, Toyota (JP); Iwao Furusawa, Kyoto (JP)

(73) Assignees: Toyota Jidosha Kabushiki Kaisha, Aichi (JP); Okayama Prefecture, Okayama (JP)

( * ) Notice: Subject to any disclaimer, the term of this patent is extended or adjusted under 35 U.S.C. 154(b) by 300 days.

(21) Appl. No.: 10/937,710

(22) Filed: Sep. 10, 2004

(65) Prior Publication Data

US 2005/0091711 A1   Apr. 28, 2005

(30) Foreign Application Priority Data

Sep. 12, 2003   (JP)   ............................. 2003-322051

(51) Int. Cl.
 C12H 15/82   (2006.01)
(52) U.S. Cl. .................................... 800/278
(58) Field of Classification Search ................ None
See application file for complete search history.

(56) References Cited

U.S. PATENT DOCUMENTS

| 5,538,878 | A | 7/1996 | Thomas et al. |
| 6,310,272 | B1 | 10/2001 | Ohashi et al. |
| 2001/0039670 | A1* | 11/2001 | Deak et al. ................... 800/279 |

FOREIGN PATENT DOCUMENTS

| EP | 0 864 650 | 9/1998 |
| EP | 1 033 405 | 9/2000 |
| EP | 1033405 A2 * | 9/2000 |
| JP | 3-32358 | 5/1991 |
| JP | 7-12312 | 2/1995 |
| JP | 7-14349 | 2/1995 |
| JP | 10-309142 | 11/1998 |
| JP | 2000-23583 | 1/2000 |
| JP | 2001-95585 | 4/2001 |
| JP | 2001-519671 | 10/2001 |
| JP | 2001-523466 | 11/2001 |
| JP | 3331367 B2 | 7/2002 |
| JP | 2002-281979 | 10/2002 |
| JP | 2002-300822 | 10/2002 |
| WO | WO 01/07592 | 2/2001 |
| WO | WO 01/20008 | 3/2001 |

OTHER PUBLICATIONS

Bowie et al 1990, Science 247:1306-1310.*
Lazar et al 1988, Mol. Cell. Biol. 8:1247-1252.*
Broun et al 1998, Science 282:1315-1317.*
Shaaltiel Y., et al., "Multienzyme Oxygen Radical Detoxifying System Correlated With Paraquat Resistance in *Conyza bonariensis*", Pesticide Biochemistry and Physiology, 26, pp. 22-28, (1986).
Shaaltiel Y., et al., "Dominant Pleiotropy Controls Enzymes Co-Segregating With Paraquat Resistance in *Conyza bonariensis*", Theor. Appl. Genet., 75, pp. 850-856, (1988).
Jansen M.A.K. et al., "Increased Tolerance to Photoinhibitory Light in Paraquat-Resistant *Conyza bonariensis* Measured by Photoacoustic Spectroscopy and $^{14}CO_2$-Fixation", Plant Physiol., 91, pp. 1174-1178, (1989).
Amsellem Z. et al., "Developmental Variability of Photooxidative Stress Tolerance in Paraquat-Resistant *Conyza*", Plant Physiol., 103, pp. 1097-1106, (1993).
Aono M. et al., "Decrease in Activity of Glutathione Reductase Enhances Paraquat Sensitivity in Transgenic *Nicotiana tabacum*", Plant Physiol., 107, pp. 645-648, (1995).
Miyagawa Y. et al., "Evaluation of the Defense System in Chloroplasts to Photooxidative Stress Caused by Paraquat Using Transgenic Tobacco Plants Expressing Catalase From *Escherichia coli*", Plant Cell Physiol., 41(3), pp. 311-320, (2000).
Deak M. et al., "Plants Ectopically Expressing the Iron-Binding Protein, Ferritin, Are Tolerant to Oxidative Damage and Pathogens", Nature Biotechnology, 17, pp. 192-196, (1999).
Tanaka K. et al., "Stress Tolerance of Transgenic *Nicotiana tabacum* with Enhanced Activities of Glutathione Reductase and Superoxide Dismutase", Biochemical Society Transactions, 24, 200S, (1996).
Aono M. et al., "Paraquat Tolerance of Transgenic *Nicotiana tabacum* With Enhanced Activities of Glutathione Reductase and Superoxide Dismutase", Plant Cell Physiol., 36(8), pp. 1687-1691, (1995).
Gupta A.S. et al., "Increased Resistance to Oxidative Stress in Transgenic Plants That Overexpress Chloroplastic Cu/Zn Superoxide Dismutase", Proc. Natl. Acad. Sci. USA, 90, pp. 1629-1633, (1993).
Wang E. et al., "Isolation and Characterization of the CYP71D16 Trichome-Specific Promoter from *Nicotiana tabacum* L.", Journal of Experimental Botany, 53(376), pp. 1891-1897, (2002).
Szymanski D.B. et al., "Control of GL2 Expression in *Arabidopsis* Leaves and Trichomes", Development, 125, pp. 1161-1171, (1998).
Database EMBL (Online), "*Arabidopsis thaliana* clone 122632 mRNA, complete sequence," created Jun. 14, 2002; Last Updated Apr. 15, 2003; Accession No. AY084949.
Database EMBL (Online), "*Arabidopsis thaliana* DNA chromosome 4, contig fragment No. 73," created Mar. 16, 2000; last updated Mar. 16, 2000; Accession No. AL161577.
Database WPI/Derwent; "Paraquat Resistant Gene and a Plasmid Vector Comprising it for Screening for a Transformed Plant," Abstract only.
Noji et al.; "Cysteine Synthase Overexpression in Tobacco Confers Tolerance to Sulfur-Containing Environmental Pollutants," Plant Physiology, Jul. 2001, 126:973-980.

(Continued)

*Primary Examiner*—David H Kruse
(74) *Attorney, Agent, or Firm*—Finnegan, Henderson, Farabow, Garrett & Dunner, LLP

(57) ABSTRACT

A paraquat resistance gene and a vascular tissue- and trichome-specific promoter are provided. The paraquat resistance gene and the vascular tissue- and trichome-specific promoter are isolated by identifying and analyzing genes of *Arabidopsis thaliana*.

15 Claims, 5 Drawing Sheets
(5 of 5 Drawing Sheet(s) Filed in Color)

OTHER PUBLICATIONS

Partial International Search Report for EP 04 02 1478, dated Jan. 3, 2005 (5 pages).

Database EMBL (Online), "*Arabidopsis thaliana* DNA chromosome 4, contig fragment No. 73," created Mar. 16, 2000; last updated Mar. 16, 2000; Accession No. ATCHRIV73.

Database EMBL (Online), "*Arabidopsis thaliana* BAC F17123," created Jun. 23, 1999; last updated Jun. 23, 1999; Accession No. AF160182.

Hermann et al., "Promoters derived banana bunchy top virus-associated components S1 and S2 drive transgene expression in both tobacco and banana," Plant Cell Rep, 20: 642-646 (2001).

Klotz et al., "Expression of the tobacco anionic peroxidase gene is tissue-specific and developmentally regulated," Plant Molecular Biology, 36: 509-520 (1998).

Rouse et al., "Promoter and expression studies on an *Arabidopsis thaliana* dehydrin gene," FEBS Letters, 381: 252-256 (1996).

European Search Report for EP 04 02 1478, dated Mar. 21, 2005 (7 pages).

* cited by examiner

A

B

C

PARAQUAT RESISTANCE GENE AND A VASCULAR TISSUE—AND TRICHOME-SPECIFIC PROMOTER

BACKGROUND OF THE INVENTION

1. Field of the Invention

The present invention relates to a paraquat resistance gene imparting paraquat resistance and a vascular tissue- and trichome-specific promoter.

2. Background Art

Plants are exposed to various environmental stresses on a regular basis including high and low temperatures, drought, high light intensity, salinity, air pollutant gases, pathogenic microbes and the like. Therefore, if useful plants that can grow sufficiently even under such types of environmental stresses such as, for example, crops, can be developed, food production will become possible even in regions in which crops and the like can not currently grow due to environmental stresses, and the possibility of being prepared for a grave food crisis that is forecast in the future will be increased. Consequently, the production of plants that have improved resistance to such kinds of environmental stresses is underway on a global basis. For example, plants have been produced that were imparted with chilling resistance (Nature, 356, 710-703, 1992; Plant Physiol., 105, 601-605, 1994), drought resistance (Plant Physiol., 107, 125-130, 1995; Nature, 379, 683-684, 1996; Nature Biotech., 17, 287-291, 1999), salt resistance (Science, 259, 508-510, 1993; Biotechnology, 14, 177-180, 1996; Plant J., 12, 133-142, 1997), air pollutants resistance (Plant Cell Physiol., 34, 129-135, 1993; Biotechnology, 12, 165-168, 1994), disease resistance (Kagaku to Seibutsu (Chemistry and Organisms), 37, 295-305, 385-392, 1999) and the like by genetic recombination techniques. Further, some plants that have been imparted with resistance to agricultural chemicals by genetic recombination techniques are in practical use (Nature, 317, 741-744, 1985; Proc. Natl. Acad. Sci. USA, 85, 391-395, 1988; EMBO J., 6, 2513-2518, 1987; EMBO J., 7, 1241-1248, 1988).

These environmental stresses are closely related with in vivo generation of active oxygen species (superoxide radical ($O_2^-$), hydrogen peroxide ($H_2O_2$), hydroxy radical ($OH^-$)). Active oxygen species are generated by respiration, photosynthesis, environmental stresses and the like, and impart fatal damage to cells by excessive oxidation of proteins, nucleic acids, membrane structure or the like. It has also been reported that an active oxygen-resistant plant produced by genetic recombination techniques showed improved resistance to the aforementioned environmental stresses (Plant Physiol., 111, 1177-1181, 1996; FEBS Letters, 428, 47-51, 1998).

To produce an active oxygen-resistant plant, a method is principally employed in which a gene of enzyme scavenging active oxygen species (superoxide dismutase, ascorbate peroxidase, catalase and glutathione reductase and the like) is introduced into the plant.

Paraquat is a non-selective and potent herbicide that can kill all plants by continuously generating active oxygens in the photosystems. Paraquat resistance can thus be used as an indicator of the resistance to active oxygens, and analysis concerning the mechanism of paraquat resistance in plants has been conducted (Pestic. Biochem. Physiol., 26, 22-28, 1986; Theor. Appl. Genet. 75, 850-856, 1988; and Plant Physiol., 91, 1174-1178, 1989).

Meanwhile, an apoptosis suppressor gene (JP Patent Publications (Kokai) No. 10-309142; No. 2000-23583; and No. 2002-300822), a gene encoding a protein homologous to aldose reductase (JP Patent Publication (Kohyo) No. 2001-523466) and a gene encoding an iron-binding protein (ferritin) (JP Patent Publication (Kohyo) No. 2001-519671) have been disclosed as genes that can impart paraquat resistance. Further, in JP Patent Publications (Kokai) No. 2002-281979 and No. 2001-95585, peroxidase derived from paraquat resistant callus is disclosed as a gene capable of imparting resistance to paraquat.

It had been believed that if a paraquat resistance gene that can impart strong resistance to paraquat could be isolated, it would be useful in the development of plants with high resistance to active oxygens generated under various kinds of environmental stress conditions (high and low temperatures, drought, high light intensity, salinity, air pollutant gases, pathogenic microbes and the like). However, recently it has been revealed that active oxygens fulfill an important role as a molecule regulating the growth and stress response of a plant. Therefore, to avoid influencing important characteristics such as crop yield, it is important to increase the resistance of a plant to stresses such as paraquat without affecting the growth and physiological control mechanisms of a plant dependent on active oxygens.

The vascular tissue is a fascicular tissue system that differentiates through each organ of pteridophytes and spermatophytes, such as the stem, leaf and root. Xylem and phloem are the components of the vascular tissue, and they function as pipes to transport water and internal substances throughout the plant. Further, the vascular cambium, which includes the interfascicular cambium and the intrafascicular cambium, is found in the vascular tissue. The vascular cambium is a site of cell proliferation, and is thus an extremely important site for the growth of a plant. Thus, the vascular tissue is a location involved in transporting water and internal substances as well as cell proliferation in a plant. Accordingly, if a gene involved in transporting water or internal substances or in cell proliferation can be introduced into a plant and expressed specifically in the vascular tissue, it will be possible to regulate the transport of water or internal substances or cell proliferation in the plant.

In addition, from the viewpoint of plant diseases, the vascular tissue is a site where a wilt disease fungus infecting plants of the family Solanaceae proliferates and transfers. When a plant virus infects a plant, the plant virus migrates a long distance from one leaf to an above leaf, and therefore the vascular tissue is also a migration site that leads to systemic infection of a plant. Accordingly, if a gene involved in proliferation or migration of a fungus or plant virus can be introduced into a plant and expressed specifically in the vascular tissue, the plant can be protected from the fungus or plant virus.

A trichome is a floccose outgrowth found on the surface of a leaf, stem, sepal and the like of a plant body. A trichome is involved in secretion and excretion from the surface of a plant body. For example, it is reported that when a plant is exposed to heavy metal (cadmium) stress, the number of trichomes on the surface of leaves increases and crystals containing cadmium or calcium adhere to the surface of the leaves, in other words, that cadmium is excreted by a trichome (Planta, 213 (1), 45-50, 2001, May). A trichome is also the site of first contact for a filamentous fungus, bacterium, insect or the like invading a plant. Further, as a defense against diseases and insect damages, for example, a fluid having antimicrobial activity and a feeding deterrent effect is secreted from a glandular hair or glandular trichome of rugosa rose of the family Rosaceae, one type of trichome. Therefore, if a gene involved in the excretion of a heavy metal or the like, or a gene involved in the secretion of a fluid having antimicrobial activity or a feeding deterrent effect can be introduced into a plant and expressed specifically in a trichome, a heavy metal can be efficiently excreted from the plant or the plant can be effectively protected against a filamentous fungus, bacterium or insect invading the plant.

As described above, it is desirable that specific gene expression be performed in a vascular tissue or trichome. As a method for performing specific gene expression, a method involving the use of a promoter exhibiting specific promoter activity in a vascular tissue or trichome can be considered. However, a promoter exhibiting promoter activity specifically in both a vascular tissue and a trichome has not been identified at present.

SUMMARY OF THE INVENTION

It is an object of the present invention to provide, for example, a paraquat resistance gene and a vascular tissue- and trichome-specific promoter by identifying and analyzing genes of *Arabidopsis thaliana*.

The present invention accomplishes the aforementioned object by providing the following.

The invention provides a gene encoding a protein of the following (a) or (b):

(a) a protein comprising the amino acid sequence represented by SEQ ID NO: 2;

(b) a protein consisting of an amino acid sequence having a substitution, deletion or addition of one or a plurality of amino acids relative to the amino acid sequence represented by SEQ ID NO: 2 and capable of imparting paraquat resistance.

The invention also provides a protein capable of imparting paraquat resistance encoded by the gene as recited above; a recombinant vector comprising the gene as recited above; a recombinant vector comprising the gene as recited above, wherein the recombinant vector further comprises a foreign gene or a foreign DNA fragment; a transformant having any one of the recombinant vectors as recited above; and a plant body having any one of the recombinant vectors as recited above and having paraquat resistance.

The invention further provides a method for screening for a transgenic plant, comprising introducing a recombinant vector into a plant; wherein the recombinant vector comprises a gene encoding a protein of the following (a) or (b):

(a) a protein comprising the amino acid sequence represented by SEQ ID NO: 2;

(b) a protein consisting of an amino acid sequence having a substitution, deletion or addition of one or a plurality of amino acids relative to the amino acid sequence represented by SEQ ID NO: 2 and capable of imparting paraquat resistance; and wherein the recombinant vector further comprises a foreign gene or a foreign DNA fragment; and screening for a transgenic plant on the basis of paraquat resistance as an indicator.

The invention also provides a method for screening for a transgenic plant, comprising introducing a recombinant vector into a plant; wherein the recombinant vector comprises a gene encoding a protein of the following (a) or (b):

(a) a protein comprising the amino acid sequence represented by SEQ ID NO: 2;

(b) a protein consisting of an amino acid sequence having a substitution, deletion or addition of one or a plurality of amino acids relative to the amino acid sequence represented by SEQ ID NO: 2 and capable of imparting paraquat resistance; and screening for a transgenic plant on the basis of paraquat resistance as an indicator.

In addition, the invention provides a vascular tissue- and trichome-specific promoter comprising DNA of the following (a), (b) or (c):

(a) DNA consisting of the nucleotide sequence represented by SEQ ID NO: 3;

(b) DNA consisting of a nucleotide sequence having a substitution, deletion or addition of one or a plurality of nucleotides relative to the nucleotide sequence represented by SEQ ID NO: 3 and capable of functioning as a vascular tissue- and trichome-specific promoter;

(c) DNA hybridizing under stringent conditions to DNA consisting of the nucleotide sequence represented by SEQ ID NO: 3 and capable of functioning as a vascular tissue- and trichome-specific promoter.

The invention also provides a recombinant vector comprising the vascular tissue- and trichome-specific promoter as recited above; a recombinant vector comprising the vascular tissue- and trichome-specific promoter as recited above, wherein the recombinant vector comprises a foreign gene or a foreign DNA fragment downstream of the vascular tissue- and trichome-specific promoter; a recombinant vector comprising the vascular tissue- and trichome-specific promoter as recited above, wherein the recombinant vector comprises a foreign gene or a foreign DNA fragment downstream of the vascular tissue- and trichome-specific promoter and wherein the foreign gene is a gene encoding a protein of the following (a) or (b):

(a) a protein comprising the amino acid sequence represented by SEQ ID NO: 2:

(b) a protein consisting of an amino acid sequence having a substitution, deletion or addition of one or a plurality of amino acids relative to the amino acid sequence represented by SEQ ID NO: 2 and capable of imparting paraquat resistance; and a transgenic plant having any one of the recombinant vectors as recited above.

BRIEF DESCRIPTION OF THE DRAWINGS

The patent or application file contains at least one drawing executed in color. Copies of this patent or patent application publication with drawings will be provided by the Office upon request and payment of the necessary fee.

DETAILED DESCRIPTION OF THE PREFERRED EMBODIMENTS

Figure 1:
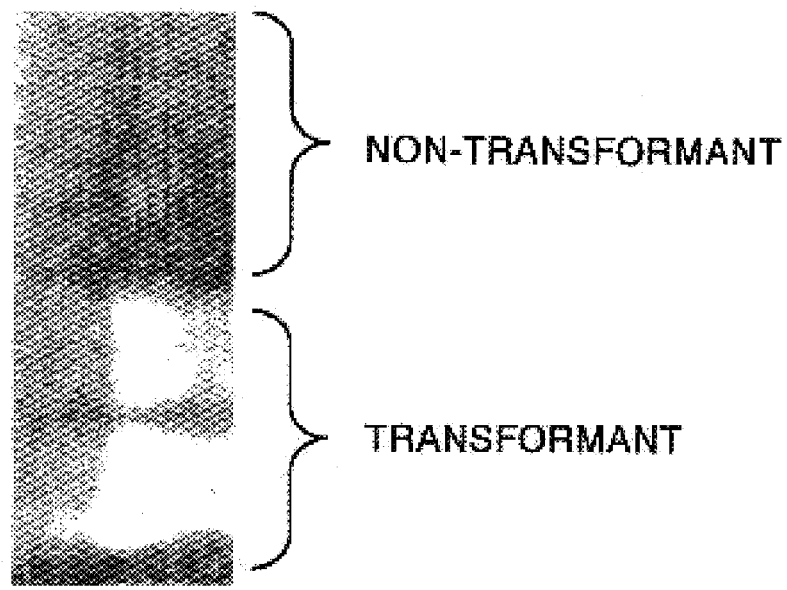
FIG. 1 is a photograph of electrophoresis of cDNA derived from an AtMVR gene transformant.

The present invention will be described in detail below.

The gene according to the present invention is a gene encoding the protein of the following (a) or (b):

(a) a protein consisting of the amino acid sequence represented by SEQ ID NO: 2; and
(b) a protein consisting of an amino acid sequence having a substitution, deletion or addition of one or a plurality of amino acids relative to the amino acid sequence represented by SEQ ID NO: 2 and imparting paraquat resistance.

The gene encoding the protein described in the above (a) is a gene (hereafter, referred to as "AtMVR gene") encoding a protein imparting paraquat resistance which consists of the amino acid sequence represented by SEQ ID NO: 2.

The present inventors performed a search on databases having the entire nucleotide sequence of *Arabidopsis thaliana* (for example, GenBank, EMBL, DDBJ, tair: The Arabidopsis Information Resource) based on the nucleotide sequence of the AtMVR gene and found that there are 13 genes homologous to the AtMVR gene (AtMVR 3-1 to AtMVR 3-13) present on the *Arabidopsis thaliana* genome. The nucleotide sequence of each of these AtMVR homologous genes and the putative amino acid sequence encoded by the relevant AtMVR homologous gene are represented by the SEQ ID NOs. listed in Table 1 below. Table 1 also lists the results of homology analysis between the AtMVR gene and each AtMVR homologous gene. The homology analysis was conducted using BLAST P at the amino acid level. Amino acids may be classified based on the chemical properties of their side chains. In the BLOSUM62 amino acid substitution matrix (Proc. Natl. Acad. Sci., 89, 10915-10919, 1992), amino acids are classified into: an amino acid with a mercapto group (C); hydrophilic amino acids that have low molecular weight (S, T, P, A, G); acidic amino acids (N, D, E, Q); basic amino acids (H, R, K); hydrophobic amino acids that have low molecular weights (M, I, L, V); and aromatic amino acids (F, Y, W). In Table 1, the term "Identities" refers to 100% correspondence in terms of amino acids and the term "Positives" refers to the numerical value when amino acids having a positive score in the BLOSUM 62 amino acid substitution matrix are added to those having 100% correspondence (see Bioinfomatics (in Japanese), Eds. Okazaki Y. & Bono H. (published by Medical Science International)).

protein encoded by the AtMVR gene has identity of 89% at the amino acid level to the protein encoded by DSA 5. It is reported that DSA 5 is a gene that expresses upon aging of the petal of lily (*Hemerocallis* hybrid cultivar) (Plant Molecular Biology 40, 237-248, 1999). However, since the protein encoded by DSA 5 has no homology with any known protein, it is unclear which functions the protein has. Accordingly, the AtMVR gene is a novel gene imparting paraquat resistance.

As used herein, the term "paraquat resistance" refers to having resistance to paraquat. More specifically, the term "paraquat-resistant plant" refers to a plant requiring a larger quantity of paraquat than a non-resistant plant in order to obtain a given effect from paraquat. Paraquat is a non-selective and potent herbicide that kills all plants by continuously generating active oxygens in the photochemical system. It is possible to confirm whether the AtMVR gene is a paraquat resistance gene imparting paraquat resistance by examining whether a transformant into which the gene was introduced can grow in the presence of paraquat.

The gene encoding the protein described in the above (b) is a gene encoding a protein consisting of an amino acid sequence having a substitution, deletion or addition of one or a plurality of amino acids (for example, 1 to 10, or 1 to 5) relative to the amino acid sequence represented by SEQ ID NO: 2 and imparting paraquat resistance.

Once the nucleotide sequence of the gene according to the present invention has been determined, it is then possible to obtain the gene according to the present invention by chemical synthesis, or by polymerase chain reaction (hereafter, referred to as "PCR") employing as a template a clone that has been cloned, or by performing hybridization employing a DNA fragment having the nucleotide sequence as a probe. Further, it is possible to synthesize a mutant of the gene according to the present invention having equivalent functions as those prior to mutation by a technique such as site-directed mutagenesis.

Examples of the method for introducing a mutation into the gene according to the present invention include a known method such as the Kunkel method or the gapped duplex method or a method in accordance with such methods. For

TABLE 1

| Name of AtMVR homologous gene | Nucleotide sequence | Amino acid sequence | Identities (%) | Positives (%) |
| --- | --- | --- | --- | --- |
| AtMVR3-1 | SEQ ID NO: 4 | SEQ ID NO: 5 | 57 | 70 |
| AtMVR3-2 | SEQ ID NO: 6 | SEQ ID NO: 7 | 55 | 69 |
| AtMVR3-3 | SEQ ID NO: 8 | SEQ ID NO: 9 | 39 | 56 |
| AtMVR3-4 | SEQ ID NO: 10 | SEQ ID NO: 11 | 39 | 55 |
| AtMVR3-5 | SEQ ID NO: 12 | SEQ ID NO: 13 | 37 | 54 |
| AtMVR3-6 | SEQ ID NO: 14 | SEQ ID NO: 15 | 36 | 52 |
| AtMVR3-7 | SEQ ID NO: 16 | SEQ ID NO: 17 | 34 | 52 |
| AtMVR3-8 | SEQ ID NO: 18 | SEQ ID NO: 19 | 34 | 51 |
| AtMVR3-9 | SEQ ID NO: 20 | SEQ ID NO: 21 | 37 | 58 |
| AtMVR3-10 | SEQ ID NO: 22 | SEQ ID NO: 23 | 25 | 44 |
| AtMVR3-11 | SEQ ID NO: 24 | SEQ ID NO: 25 | 33* | 51* |
| AtMVR3-12 | SEQ ID NO: 26 | SEQ ID NO: 27 | 25 | 41 |
| AtMVR3-13 | SEQ ID NO: 28 | SEQ ID NO: 29 | 22 | 41 |

*The comparison with AtMVR3-11 shows the homology result for comparison with a partial sequence of AtMVR3-11.

As shown in Table 1, the homology of AtMVR with the 13 AtMVR homologous genes ranged from 22 to 57% for Identities and from 41 to 70% for Positives. These AtMVR homologous genes are considered to impart paraquat resistance in the same manner as the AtMVR gene.

Further, the AtMVR gene has homology to a senescence-associated protein, DSA 5 (GenBank accession number AF082030) (Plant Molecular Biology 40, 237-248, 1999). The result of homology analysis using BLAST X showed the example, introduction of a mutation can be performed using a kit for introducing a mutation (for example, Mutant-K (manufactured by TAKARA, Inc.), or Mutant-G (manufactured by TAKARA, Inc.)) utilizing site-directed mutagenesis or using LA PCR in vitro Mutagenesis series kit manufactured by TAKARA, Inc.

A protein imparting paraquat resistance according to the present invention is the protein encoded by the gene according to the present invention. For example, the gene according to the present invention is integrated into a vector derived from *Escherichia coli* or the like, and *E. coli* is then transformed with the obtained recombinant vector. Thereafter, the protein according to the present invention can be obtained by extracting the protein synthesized within *E. coli*.

Further, a recombinant vector according to the present invention is a recombinant vector comprising the gene according to the present invention. The recombinant vector according to the present invention can be obtained by inserting the gene according to the present invention into an appropriate vector. A vector used for inserting the gene according to the present invention is not particularly limited as long as it is capable of replication within a host, and examples thereof include a plasmid, a shuttle vector, and a helper plasmid. In addition, when the vector itself is not capable of replication, a DNA fragment that is capable of replication by a method such as insertion into the chromosome of a host may be used.

Examples of plasmid DNA include a plasmid derived from *E. coli* (pBI221 and the like, for example, pET system such as pET30b, pBR system such as pBR322 and pBR325, pUC system such as pUC118, pUC119, pUC18 and pUC19, pBluescript, and pBI221), a plasmid derived from *Bacillus subtilis* (for example, pUB110 and pTP5), a binary plasmid derived from *Agrobacterium tumefaciens* (for example, pBI system derived from pBIN19, pBI101, or pBI121), a plasmid derived from yeast (for example, YEp system such as YEp13, or YCp system such as YCp50) or the like. Examples of phage DNA include λ phage (Charon 4A, Charon 21A, EMBL3, EMBL4, λgt10, λgt11, λZAP and the like). Further, an animal virus vector such as retrovirus or vaccinia virus, a plant virus vector such as cauliflower mosaic virus, or an insect virus vector such as baculovirus can also be used.

To insert the gene according to the present invention into a vector, a method may be used in which cDNA of the gene according to the present invention is first cleaved using an appropriate restriction enzyme and then inserted into a restriction enzyme site or multicloning site of an appropriate vector DNA and ligated into the vector. Further, a method may be used in which a homologous region is respectively provided in one part of a vector and cDNA of the gene according to the present invention, and the vector and the cDNA are connected by an in vitro method using PCR or the like or an in vivo method using yeast or the like.

A recombinant vector according to the present invention can also include a foreign gene or a foreign DNA fragment in addition to the gene according to the present invention. A method for inserting a foreign gene or a foreign DNA fragment into a vector is the same as the method for inserting a DNA fragment according to the present invention into a vector. Any gene or DNA fragment may be used as a foreign gene or a foreign DNA fragment. Thus, the gene according to the present invention can be used as a selective marker gene to indicate paraquat resistance, for example, as with an antibiotic resistance gene for kanamycin or hygromycin or the like.

A transformant according to the present invention is a transformant having the recombinant vector according to the present invention. The transformant according to the present invention can be obtained by introducing the recombinant vector according to the present invention into a host. A host is not particularly limited as long as it is capable of expressing the gene according to the present invention, however a plant is preferred. When the host is a plant, it is possible to obtain a transgenic plant in the manner described below.

A "plant" to be transformed in the present invention may be any of: a whole plant, a plant organ (for example, leaf, petal, stem, root, or seed), plant tissue (for example, epidermis, phloem, parenchyma, or xylem) or a plant culture cell.

Examples of the plant that can be used in the transformation include, but are not limited to, a plant belonging to the family Poaceae, Brassicaceae, Solanaceae, or Leguminosae (see below).

Poaceae: *Oryza sativa, Zea mays*
Brassicaceae: *Arabidopsis thaliana*
Solanaceae: *Nicotiana tabacum*
Leguminosae: *Glycine max*

The recombinant vector according to the present invention can be introduced into a plant by a conventional transformation method such as, for example, the electroporation method, *Agrobacterium* method, particle gun method, or PEG method.

For example, when using the electroporation method, the recombinant vector according to the present invention is introduced into a host by conducting the treatment using an electroporation apparatus equipped with a pulse controller under conditions of a voltage of 500 to 1600 V, at 25 to 1000 μF, for 20 to 30 msec.

When using the particle gun method, the whole plant, a plant organ or plant tissue itself may be used without any treatment, a section thereof may be prepared and then used, or protoplast may be prepared and used. The prepared sample can then be treated using a gene transfer device (for example, PDS-1000/He manufactured by Bio-Rad Inc.). Although the treatment conditions may vary depending on the plant or sample used, the treatment is normally conducted at a pressure of approximately 450 to 2000 psi and a distance of approximately 3 to 12 cm.

A method using the Ti plasmid or Ri plasmid of *Agrobacterium* takes advantage of a characteristic whereby, when a bacterium belonging to the genus *Agrobacterium* infects a plant, one part of plasmid DNA possessed by the bacterium is transferred into the genome of the plant. This method can thus be used to introduce the gene according to the present invention into a plant host. Among the bacteria belonging to the genus *Agrobacterium*, when *Agrobacterium tumefaciens* infects a plant, it causes the formation of a tumor that is referred to as "crown gall." Further, when *Agrobacterium rhizogenes* infects a plant, it incites generation of a capillary root. These are caused by a region referred to as a "T-DNA (Transferred DNA) region" of a Ti plasmid or Ri plasmid transferring into a plant at the time of infection to be integrated into the genome of the plant. Accordingly, the DNA to be integrated into a plant genome is first inserted into the T-DNA region of a Ti plasmid or Ri plasmid, and then the DNA can be integrated into the plant genome by infecting the plant host with a bacterium of the genus *Agrobacterium*.

Examples of the method for transforming a bacterium of the genus *Agrobacterium* into a plant host include the above described electroporation method, patent gun method and PEG method, as well as an in planta method. Examples of the in planta method include a direct *Agrobacterium* inoculation method and an infiltration method.

Tumor tissue or shoot, capillary root or the like obtained as the result of the transformation can be used without any treatment for cell culture, tissue culture or organ culture. Alternatively, it can be regenerated in a plant body by administration of a plant hormone (auxin, cytokinin, gibberellin, abscisic acid, ethylene, brassinolide or the like) of an appropriate concentration using a conventional plant tissue culture method.

The gene according to the present invention may also be introduced into a plant by utilizing a plant virus as a vector. Examples of the plant virus that can be used include cauliflower mosaic virus. First, the viral genome is inserted into a vector derived from *E. coli* or the like to produce a recombinant, and then the gene according to the present invention is inserted into the viral genome. The viral genome modified in this manner is subsequently cleaved from the recombinant using a restriction enzyme, and the gene according to the present invention can then be introduced into a plant host by inoculating the viral genome into the plant host.

In addition to introduction into a plant host as described above, the recombinant vector according to the present invention may also be introduced into bacteria belonging to the genus *Escherichia* such as *E. coli*, the genus *Bacillus* such as *Bacillus subtilis*, or the genus *Pseudomonas* such as *Pseudomonas putida*, as well as yeast such as *Saccharomyces cerevisiae* and *Schizosaccharomyces pombe*, animal cells such as COS cell or CHO cell, and insect cells such as Sf9. When using a bacterium such as *E. coli* or yeast or the like as a host, it is preferable that the recombinant vector according to the present invention is capable of autonomous replication in the bacterium and that it is comprised of a promoter, a ribosome binding sequence, a transcription termination sequence and the gene according to the present invention. It may also comprise a gene regulating the promoter.

The method for introducing the recombinant vector according to the present invention into a bacterium is not particularly limited as long as it is a method that can introduce DNA into a bacterium, and for example a method using calcium ion or the electroporation method may be mentioned.

The method for introducing the recombinant vector according to the present invention into yeast is not particularly limited as long as it is a method that can introduce DNA into yeast, and for example the electroporation method, spheroplast method and lithium acetate method may be mentioned.

When using an animal cell as a host, monkey cell COS-7, Vero, Chinese hamster ovary cell (CHO cell), mouse L-cells or the like can be used. The method for introducing the recombinant vector according to the present invention into an animal cell is not particularly limited as long as it is a method that can introduce DNA into an animal cell, and for example the electroporation method, calcium phosphate method and lipofection method may be mentioned.

When using an insect cell as a host, an Sf9 cell or the like can be used. The method for introducing the recombinant vector according to the present invention into an insect cell is not particularly limited as long as it can introduce DNA into an insect cell, and for example the calcium phosphate method, lipofection method and electroporation method may be mentioned.

It is possible to confirm whether or not the gene according to the present invention has been integrated into a host by using the PCR method, Southern hybridization method, Northern hybridization method or the like. For example, PCR can be conducted after preparing DNA from the transformant and designing a DNA-specific primer. Next, the amplification product is subjected to agarose gel electrophoresis, polyacrylamide gel electrophoresis or capillary electrophoresis or the like, and the product thereof is then stained with ethidium bromide, SYBR Green solution or the like. Thereafter, whether or not transformation has occurred can be confirmed by the detection of the amplification product as a single band. It is also possible to detect the amplification product after conducting PCR using a primer that has been labeled previously with a fluorescent dye or the like. In addition, a method may be employed in which the amplification product is bound to a solid phase of a microplate or the like to enable confirmation of the amplification product by fluorescence or enzyme reaction or the like.

A plant body according to the present invention is one having a recombinant vector comprising the gene according to the present invention and having paraquat resistance. As used herein, the term "plant body" refers to a whole plant transformed with a recombinant vector comprising the gene according to the present invention. The plant body according to the present invention can be obtained by introducing the above recombinant vector into a plant cell or the like and regenerating a transgenic plant body from the obtained transgenic plant cell. As a regeneration method, a method may be employed in which transformed cells in a callus form are transferred to a culture medium in which the type and concentration of hormones have been modified and allowed to culture, and an adventitious embryo is allowed to form to obtain a complete plant body. Examples of the culture medium to be used include LS medium and MS medium. Introduction of a recombinant vector into a plant cell or the like can be performed by a method similar to the method described above.

In the plant body according to the present invention, a protein imparting paraquat resistance that is encoded by the gene according to the present invention is overexpressed throughout the whole plant body. Thus, the plant body according to the present invention can have resistance to paraquat.

A method of screening for transgenic plants according to the present invention is a method in which the recombinant vector according to the present invention is introduced into plants and paraquat resistance is used as an indicator to screen for transgenic plants. Transformation can be verified by employing the gene according to the present invention as a selective marker gene to indicate paraquat resistance. Examples of the screening method include a method in which plants transformed by the recombinant vector according to the present invention are grown in a paraquat-containing medium and the screening is carried out based on variations in the life and death as well as growth of the plants. The concentration of paraquat used for the screening may vary depending on the species and size of plants and the like, however, for example, when *Arabidopsis thaliana* is used as a host, paraquat may be present in a medium at a concentration of preferably 0.1 to 3.0 μM, more preferably 1.0 to 3.0 μM, and most preferably 3.0 μM. A non-transgenic plant, i.e., a wild-type plant, develops chlorosis and dies in a paraquat-containing medium. In contrast, a plant transformed with the recombinant vector according to the present invention remains green even in a paraquat-containing medium. Thus, it is possible to verify a clear difference in growth in a paraquat-containing medium between a non-transgenic plant and a plant transformed with the recombinant vector according to the present invention.

When employing antibiotic resistance or herbicide resistance as an indicator, false positivity may be observed at the screening stage because of the existence of a difference in sensitivity among the plant. In contrast, paraquat is a nonselective and potent herbicide that can kill all plants. Consequently, in the method of screening transgenic plants according to the present invention, false positivity is not observed in the screening stage. Further, according to the method of screening transgenic plants according to the present invention, resistance can be effectively confirmed at an early stage of growth.

The promoter according to the present invention is a vascular tissue- and trichome-specific promoter comprising the DNA of the following (a), (b) or (c):

(a) DNA consisting of the nucleotide sequence represented by SEQ ID NO: 3;

(b) DNA consisting of a nucleotide sequence having a substitution, deletion or addition of one or a plurality of nucleotides relative to the nucleotide sequence represented by SEQ ID NO: 3 and functioning as a vascular tissue- and trichome-specific promoter; and (c) DNA hybridizing under stringent conditions to DNA consisting of the nucleotide sequence represented by SEQ ID NO: 3 and functioning as a vascular tissue- and trichome-specific promoter.

The vascular tissue- and trichome-specific promoter described in the above (a) is a vascular tissue- and trichome-specific promoter found in an untranslated region on the 5'-upstream side of the AtMVR gene and consists of the nucleotide sequence represented by SEQ ID NO: 3. The promoter described in (a) can be determined by performing a search based on approximately 3,000 nucleotides on the 5'-upstream side of the AtMVR gene on a database having the complete nucleotide sequence for *Arabidopsis thaliana*.

As used herein, the term "vascular tissue- and trichome-specific promoter" refers to a promoter exhibiting activity specific to a vascular tissue and trichome of a plant. The term "vascular tissue" refers to a fascicular tissue system that differentiates through each organ of pteridophytes and spermatophytes, such as the stem, leaf, and root. Xylem and phloem are the components of the vascular tissue, and they function as pipes to transport water and internal substances throughout the plant. Meanwhile, the term "trichome" refers to a floccose outgrowth existing on the surface of a leaf, stem, or sepal of a plant body. A trichome participates in secretion and excretion from the plant body surface.

The activity of a vascular tissue- and trichome-specific promoter can be determined in accordance with a conventional method. For example, an expression vector having a reporter gene operably linked thereto downstream of a promoter may be constructed. Next, an appropriate plant is transformed with the expression vector. The obtained transformant is then cultured under predetermined conditions, and the expression amount of the reporter gene in a vascular tissue and trichome may be determined at the mRNA or protein level to enable the measurement of promoter activity under the relevant conditions. Further, when the reporter gene is the β-Glucuronidase (GUS) gene, the specificity of promoter activity in a vascular tissue and trichome can be determined by observing the histochemical coloring caused by the expressed GUS.

For example, as a method of the histochemical coloring using GUS, a method may be mentioned in which a reaction mixture containing 5-brome-4-chloro-3-indolyl-β-D-glucuronide (X-Gluc) as a GUS substrate is added to a tissue of a transformant in which the GUS gene has been introduced. When the GUS gene is expressed, X-Gluc is de-esterified to generate an indoxyl derivative monomer, and this monomer is oxidation-polymerized with air to form a blue indigotin pigment. In a transformed cell or tissue, this blue pigment accumulates to exhibit a blue color.

Further, a specified untranslated region on the 5'-upstream side of the AtMVR gene can be readily obtained by conducting PCR employing genome extracted from *Arabidopsis thaliana* as a template and using primers that are complementary to the nucleotide sequences on both ends of the region.

The promoter according to the present invention may be the nucleotide sequence represented by SEQ ID NO: 3, more specifically, the entire untranslated region on the 5'-upstream side, or it may be one part of DNA consisting of the nucleotide sequence represented by SEQ ID NO: 3 in so far as it exhibits a function as a vascular tissue- and trichome-specific promoter.

The vascular tissue- and trichome-specific promoter described in the above (b) consists of a nucleotide sequence having a substitution, deletion or addition of one or a plurality of nucleotides (for example, 1 to 10, or 1 to 5) relative to the nucleotide sequence represented by SEQ ID NO: 3 and functions as a vascular tissue- and trichome-specific promoter.

The vascular tissue- and trichome-specific promoter described in the above (c) hybridizes under stringent conditions to DNA consisting of the nucleotide sequence represented by SEQ ID NO: 3 and functions as a vascular tissue- and trichome-specific promoter.

As used herein, the term "stringent conditions" refers to, for example, when using probe DNA labeled with phosphorus-32, hybridization in a hybridization solution consisting of 5×SSC (0.75 M NaCl, 0.75 M sodium citrate), 5× Denhardt's reagent (0.1% Ficoll, 0.1% polyvinylpyrrolidone, 0.1% bovine serum albumin) and 0.1% sodium dodecyl sulphate (SDS) at a temperature between 45 and 68° C., preferably 60 to 68° C. Further, in the washing step, washing is performed in a washing solution consisting of 2×SSC and 0.1% SDS at a temperature between 45 and 55° C., and more preferably in a washing solution consisting of 0.1×SSC and 0.1% SDS at a temperature between 45 and 55° C. When using probe DNA enzymatically labelled using the AlkPhos direct labeling module kit (Amersham Biotech), hybridization may be conducted in a hybridization solution (containing 0.5 M NaCl and 4% blocking reagent) having the composition described in the manual accompanying the kit at a temperature between 55 to 75° C. Further, in a washing step, washing may be conducted in a primary washing solution (containing 2 M urea) in accordance with the instructions in the manual accompanying the kit at a temperature between 55 to 75° C., and in a secondary washing solution at room temperature. Other detection techniques may also be used, in which case the conditions may be the standard conditions for the relevant detection technique.

Once the nucleotide sequence of the promoter according to the present invention has been determined, it is then possible to obtain the promoter according to the present invention by chemical synthesis, or by PCR employing a cloned probe as a template, or by performing hybridization employing a DNA fragment having the nucleotide sequence as a probe. Further, it is possible to synthesize a mutant of the promoter according to the present invention having equivalent functions as those prior to mutation by a technique such as site-directed mutagenesis.

Examples of the method for introducing a mutation into the promoter according to the present invention include a known method such as the Kunkel method or the gapped duplex method or a method in accordance with such methods. For example, the introduction of a mutation can be performed using a kit for introducing a mutation (for example, Mutant-K or Mutant-G (both manufactured by TAKARA, Inc.) utilizing site-directed mutagenesis or using LA PCR in vitro Mutagenesis series kit manufactured by TAKARA, Inc.

A recombinant vector according to the present invention comprising the promoter according to the present invention can be obtained by inserting the promoter according to the present invention into an appropriate vector. A vector for inserting the promoter according to the present invention is not particularly limited as long as it is capable of replication within a host, and examples thereof include a plasmid, a shuttle vector, and a helper plasmid. In addition, when the vector itself is not capable of replication, a DNA fragment that is capable of replication by a method such as insertion into the chromosome of a host may be used.

Examples of plasmid DNA include a plasmid derived from *E. coli* (pBI221 and the like, for example, pET system such as pET30b, pBR system such as pBR322 and pBR325, pUC system such as pUC118, pUC119, pUC18 and pUC19, pBluescript, and pBI221), a plasmid derived from *Bacillus subtilis* (for example, pUB110 and pTP5), a binary plasmid derived from *Agrobacterium tumefaciens* (for example, pBI system derived from pBIN19, pBI101, or pBI121), a plasmid derived from yeast (for example, YEp system such as YEp13, or YCp system such as YCp50) or the like. Examples of phage DNA include λ phage (Charon 4A, Charon 21A, EMBL3, EMBL4, λgt10, λgt11, λZAP and the like). Further, an animal virus vector such as retrovirus or vaccinia virus, or an insect virus vector such as baculovirus can also be used.

To insert the promoter according to the present invention into a vector, a method may be used in which purified DNA is first cleaved with an appropriate restriction enzyme and then inserted into a restriction enzyme site or multicloning site of an appropriate vector DNA and ligated to the vector. Further, a method may also be used in which a homologous region is respectively provided in one part of a vector and the promoter according to the present invention, and the vector and promoter are ligated by an in vitro method using PCR or the like or an in vivo method using yeast or the like.

The recombinant vector according to the present invention comprising the promoter according to the present invention can further include a foreign gene or a foreign DNA fragment that is inserted downstream of the promoter according to the present invention. A method for inserting a foreign gene or a foreign DNA fragment is the same as a method for inserting the promoter according to the present invention into a vector.

In the recombinant vector according to the present invention comprising the promoter according to the present invention, examples of a foreign gene to be inserted downstream of the promoter according to the present invention include any foreign gene, and specific examples include a gene involved in transport of water or internal substances or in cell proliferation, a gene involved in proliferation or transport of bacteria or a plant virus, a gene involved in discharge of a heavy metal or the like, or a gene involved in secretion of a liquid having antimicrobial activity or a feeding deterrent effect. More specifically, the gene may be a gene for transporter or pump, a gene encoding a PR-protein (Pathogenesis related protein) (chitinase, peroxidase or the like), a defensin family gene, a phytoalexin synthesis gene or a repellant pheromone synthesis gene of a pest insect or the like. As further examples of a foreign gene, the gene according to the present invention described above, the AtMVR gene, may be mentioned.

Examples of the foreign DNA fragment to be inserted downstream of the promoter according to the present invention include antisense RNA or a ribozyme in which the RNA itself is functioning.

The transgenic plant according to the present invention is a transgenic plant having the recombinant vector according to the present invention comprising the promoter according to the present invention. The transgenic plant according to the present invention can be obtained by introducing the recombinant vector according to the present invention comprising the promoter according to the present invention into a plant. A transgenic plant can be obtained in the manner described below.

A "plant" to be transformed in the present invention may be any of: a whole plant, a plant organ having a vascular tissue and/or trichome (for example, leaf, petal, stem, root, or seed), plant tissue (for example, epidermis, phloem, parenchyma, or xylem) or a plant culture cell. Examples of the plant that can be used in the transformation include, but are not limited to, a plant belonging to the family Poaceae, Brassicaceae, Solanaceae, or Leguminosae (see below).

Poaceae: *Oryza sativa*, *Zea mays*
Brassicaceae: *Arabidopsis thaliana*
Solanaceae: *Nicotiana tabacum*
Leguminosae: *Glycine max*

The recombinant vector according to the present invention comprising the promoter according to the present invention can be introduced into a plant by a conventional transformation method such as, for example, the electroporation method, *Agrobacterium* method, particle gun method, or PEG method.

For example, when using the electroporation method the recombinant vector according to the present invention comprising the promoter according to the present invention is introduced into a host by the treatment using an electroporation apparatus equipped with a pulse controller under conditions of a voltage of 500 to 1600 V, at 25 to 1000 µF, for 20 to 30 msec.

When using the particle gun method, the whole plant, a plant organ or plant tissue itself may be used without any treatment, a section thereof may be prepared and then used, or protoplast may be prepared and used. The prepared sample can then be treated using a gene transfer device (for example, PDS-1000/He manufactured by Bio-Rad Inc.). Although the treatment conditions may vary depending on the plant or sample used, the treatment is normally conducted at a pressure of approximately 450 to 2000 psi and a distance of approximately 3 to 12 cm.

The method using the Ti plasmid or Ri plasmid of *Agrobacterium* takes advantage of a characteristic whereby, when a bacterium belonging to the genus *Agrobacterium* infects a plant, one part of plasmid DNA possessed by the bacterium is transferred into the genome of the plant. This method can thus be used to introduce the promoter according to the present invention and a foreign gene or foreign DNA fragment into a plant host. Among the bacteria belonging to the genus *Agrobacterium*, when *Agrobacterium tumefaciens* infects a plant, it causes the formation of a tumor that is referred to as "crown gall." Further, when *Agrobacterium rhizogenes* infects a plant, it incites the generation of a capillary root. These are caused by a region referred to as a "T-DNA (Transferred DNA) region" of a Ti plasmid or Ri plasmid transferring into a plant at the time of infection to be integrated into the genome of the plant. Accordingly, the DNA to be integrated into a plant genome is first inserted into the T-DNA region of a Ti plasmid or Ri plasmid, and then the DNA can be integrated into the plant genome by infecting the plant host with a bacterium of the genus *Agrobacterium*.

Examples of the method for transforming a bacterium of the genus *Agrobacterium* into a plant host include the above described electroporation method, particle gun method and PEG method, as well as an in planta method. Examples of the in planta method include a direct *Agrobacterium* inoculation method and an infiltration method.

The tumor tissue or shoot, capillary root or the like obtained as the result of transformation can be used without any treatment for cell culture, tissue culture or organ culture. Alternatively, it can be regenerated in a plant body by administration of a plant hormone (auxin, cytokinin, gibberellin, abscisic acid, ethylene, brassinolide or the like) of an appropriate concentration using a plant tissue culture method known in the prior art.

Further, the promoter according to the present invention and a foreign gene or foreign DNA fragment can be introduced into a plant by utilizing a plant virus as a vector. Examples of the plant virus that can be used herein include cauliflower mosaic virus. First, the viral genome is inserted into a vector derived from *E. coli* or the like to produce a recombinant, and then the promoter according to the present invention and the foreign gene or foreign DNA fragment is inserted into the viral genome. The viral genome modified in this manner is subsequently cleaved from the recombinant using a restriction enzyme, and the promoter according to the present invention and the foreign gene or foreign DNA fragment can be introduced into a plant host by inoculating the viral genome into the plant host.

The transgenic plant according to the present invention produced in the above manner can specifically express the foreign gene or foreign DNA fragment in a vascular tissue and trichome using the promoter according to the present invention.

The vascular tissue is a location involved in transporting water and internal substances as well as cell proliferation in a plant. Thus, when a gene involved in transporting water or internal substances or in cell proliferation is introduced as a foreign gene into the transgenic plant according to the present invention, the transport of water and internal substances or cell proliferation in the plant can be regulated. The vascular tissue is also a site where wilt disease fungus infecting plants of the family Solanaceae proliferates and transfers. When a plant virus infects a plant, the plant virus migrates a long distance from one leaf to an above leaf and therefore the vascular tissue is also a migration site that leads to systemic infection of a plant. Thus, when a gene involved in proliferation or migration of a fungus or plant virus is introduced as a foreign gene into the transgenic plant according to the present invention, the plant can be protected from the fungus or plant virus.

Meanwhile, a trichome is involved in secretion and excretion from the surface of a plant body. For example, it is reported that when a plant is exposed to heavy metal (cadmium) stress, the number of trichomes on the surface of leaves increases and crystals containing cadmium or calcium adhere to the surface of the leaves, in other words, that cadmium is excreted by a trichome (Planta, 213 (1), 45-50, 2001, May). A trichome is also the site of first contact for a filamentous fungus, bacterium, insect or the like invading a plant. Further, as a defense against diseases and insect damages, for example, a fluid having antimicrobial activity and a feeding deterrent effect is secreted from a glandular hair or glandular trichome of rugosa rose of the family Rosaceae, one type of trichome. Therefore, when a gene involved in the excretion of a heavy metal or the like, or a gene involved in secretion of a fluid having antimicrobial activity or a feeding deterrent effect is introduced as a foreign gene into the transgenic plant according to the present invention, heavy metal can be efficiently excreted from the plant or the plant can be effectively protected against a filamentous fungus, bacterium or insect invading the plant.

Further, when the gene according to the present invention is introduced as a foreign gene into the transgenic plant according to the present invention, resistance to paraquat can be imparted by promoting the transportation and excretion and the like of paraquat incorporated in the plant body.

EXAMPLES

The present invention will be explained in detail further below with reference to the following examples. However, the examples are not intended to limit the technical scope of the invention.

Example 1

Isolation of Paraquat Resistance Gene

In this example, Weigel T-DNA lines acquired from Nottingham *Arabidopsis* Stock Center (School of Biosciences, University of Nottingham, Sutton Bonington Campus, Loughborough, LE12 5RD, United Kingdom) were used as activation tag lines of *Arabidopsis thaliana*.

(1) Screening of Individuals Capable of Growing in Paraquat-containing Medium Using Activation-tagged Lines of *Arabidopsis thaliana* (Weigel T-DNA Lines)

Seeds of Weigel T-DNA lines were sterilely inoculated in ½ MS agar (1%) culture medium (2.3 g/l of Murashige and Skoog Plant Salt Mixture (manufactured by Wako Pure Chemical Industries Ltd.), 1.5 mg/l of thiamine hydrochloride, 2.5 mg/l of nicotinic acid, 0.25 mg/l of pyridoxine hydrochloride, 1.5% of sucrose, 1% of agar) containing 3 μM of paraquat (methyl viologen, manufactured by Sigma Chemical Co.), and cultured at 22° C. under irradiation of light of 60 μE/m$^2$/s (cycle of 16 hrs photoperiod/8 hrs dark period). Approximately 10 days after culture, individuals growing in the paraquat-containing medium were screened.

(2) Estimation of Insertion Sites of T-DNA from the Screened Activation-tagged Lines by the TAIL-PCR Method Seeds of Weigel T-DNA lines from which screened individuals originated were planted in a pot containing vermiculite (manufactured by Asahi Kagaku Kogyo Co., Ltd.) and grown for approximately one month at 23° C. under a light intensity of 100 μE/m$^2$/s with a photoperiod condition of 16 hrs photoperiod/8 hrs dark period.

Genome DNA was prepared from leaves of cultivated individuals using the DNeasy Plant Mini Kit (manufactured by QIAGEN), and three types of specific primers (TL1: SEQ ID NO: 31; TL2: SEQ ID NO: 32; TL3: SEQ ID NO: 33) were designed for the vicinity of a T-DNA left sequence (T-DNA left border: SEQ ID NO: 30) of an activation-tagging vector (pSKI015: GenBank accession No. AF187951) used with the Weigel T-DNA lines. TAIL-PCR (Shokubutsu No PCR Jikken Purotokoru (Protocols of PCR Experiments for Plants), (Eds. Shimamoto K. & Sasaki T.), New Edition, 2000, pp 83-89, Shujunsha Co., Ltd., Tokyo; Genomics, 25, 674-681, 1995; Plant J., 8, 457-463, 1995) was then performed using the specific primers and a random primer 1 (SEQ ID NO: 34) and the PCR reaction mixture and reaction conditions described below to amplify genome DNA bordering the T-DNA. In SEQ ID NO: 34, n represents a, g, c, or t (location: 1 and 11), s represents g or c (location: 7), and w represents a or t (location: 8 and 13).

The composition of the reaction mixture and the PCR conditions for the first-round PCR are listed in tables 2 and 3.

TABLE 2

| | |
|---|---|
| Template (genome DNA): | 10 ng |
| 10x PCR buffer (manufactured by TAKARA BIO Inc.): | 2 μl |
| 2.5 mM dNTPs (manufactured by TAKARA BIO Inc.): | 1.6 μl |
| First specific primer (TL1: SEQ ID NO: 31): | 3 pmol |
| Random primer 1 (SEQ ID NO: 34): | 80 pmol |
| AmpliTaq (manufactured by Applied Biosystems): | 0.8 units |
| Total volume | 20 μl |

TABLE 3

1: 94° C. (1 min)/95° C. (1 min)
2: 94° C. (1 min)/65° C. (1 min)/72° C. (3 min) × 5 cycles
3: 94° C. (1 min)/25° C. (3 min) → to 72° C. at 3 min/72° C. (3 min) × 1 cycle
4: 94° C. (30 sec)/68° C. (1 min)/72° C. (3 min)
    94° C. (30 sec)/68° C. (1 min)/72° C. (3 min)
    94° C. (30 sec)/44° C. (1 min)/72° C. (3 min) × 14 cycles
5  72° C. (5 min)

The composition of the reaction mixture and the PCR conditions for the second-round PCR are listed in tables 4 and 5.

TABLE 4

| | |
|---|---|
| Template (a 50-fold dilution of product of first-round PCR): | 1 µl |
| 10x PCR buffer: | 2 µl |
| 250 µM dNTPs: | 2 µl |
| Second specific primer (TL2: SEQ ID NO: 32): | 4 pmol |
| Random primer 1 (SEQ ID NO: 34): | 60 pmol |
| AmpliTaq: | 0.6 units |
| Total volume | 20 µl |

TABLE 5

| | |
|---|---|
| #6: | 94° C. (30 sec)/64° C. (1 min)/72° C. (3 min) |
| | 94° C. (30 sec)/64° C. (1 min)/72° C. (3 min) |
| | 94° C. (30 sec)/44° C. (1 min)/72° C. (3 min) × 10 cycles |
| #5 | 72° C. (5 min) |

The composition of the reaction mixture and the PCR conditions for the third-round PCR are listed in tables 6 and 7.

TABLE 6

| | |
|---|---|
| Template (a 50-fold dilution of product of second-round PCR): | 1 µl |
| 10x PCR buffer: | 10 µl |
| 2.5 mM dNTPs: | 1 µl |
| Third specific primer (TL3: SEQ ID NO: 33): | 30 pmol |
| Random primer 1 (SEQ ID NO: 34): | 300 pmol |
| AmpliTaq: | 3 units |
| Total volume | 100 µl |

TABLE 7

| | |
|---|---|
| #7: | 94° C. (1 min)/44° C. (1 min)/72° C. (3 min) × 20 cycles |
| #5 | 72° C. (5 min) |

Next, after subjecting the reaction products from the second-round PCR and third-round PCR to electrophoresis on agarose gel, the presence or absence of amplification and the specificity of the reaction products were verified.

Further, using the specific primer TL3 (SEQ ID NO: 33), the amplification product of the third-round PCR was directly sequenced using the ABI PRISM Dye Terminator Cycle Sequencing Kit (Applied Biosystems) and the nucleotide sequence was then determined using the ABI PRISM 310 genetic analyzer (Applied Biosystems). As a result, 278-bp sequence information was obtained (SEQ ID NO: 35). In SEQ ID NO: 35, n represents a, g, c, or t (location: 13, 35, 73, 108, 156, 190, 198 and 201). A search was performed for the obtained sequence on databases having the entire nucleotide sequence of *Arabidopsis thaliana*, and it was found that the insertion site is located at 77240 bp of BAC clone F17123.

(3) Isolation of cDNA of Paraquat Resistance Gene

Seeds of *Arabidopsis thaliana* (*Arabidopsis thaliana* ecotype Columbia (Col-0)) were planted in a pot containing vermiculite (Asahi Kagaku Kogyo Co., Ltd.) and allowed to grow for approximately one month at 23° C. under a light intensity of 100 µE/m²/s with a photoperiod condition of 16 hrs photoperiod/8 hrs dark period.

After growing, leaves of individuals were frozen using liquid nitrogen. Subsequently, total RNA was extracted using the RNeasy Plant Mini Kit (manufactured by QIAGEN). Thereafter, cDNA was synthesized from the extracted total RNA using the ProSTAR First Strand RT-PCR Kit (manufactured by STRATAGEN).

Based on the sequence of a putative open reading frame (ORF) gene present within an adjacent 10 kb of a structural gene having the nucleotide sequence (SEQ ID NO: 35) obtained in the above (2), a primer 141dF (SEQ ID NO: 36) and a primer 141dR (SEQ ID NO: 37) were designed for the putative structural gene, and PCR was then performed using these primers and the following reaction mixture (Table 8) containing Takara EX-Taq (manufactured by TAKARA BIO Inc.) employing the above synthesized cDNA as a template.

TABLE 8

| | |
|---|---|
| Template (cDNA): | 50 ng |
| 10x Ex Taq buffer (TAKARA BIO Inc.): | 2 µl |
| dNTPs: | 200 µM |
| Each primer: | 0.2 µM |
| Takara EX-Taq: | 1 unit |
| Total volume | 20 µl |

Thirty cycles of 94° C. (30 sec)/55° C. (30 sec)/72° C. (60 sec) were employed as the reaction conditions.

The amplification product was cloned into the pGEM-T Easy vector (manufactured by Promega), and the nucleotide sequence was then determined using the ABI PRISM 310 genetic analyzer (Applied Biosystems). As a result, a cDNA fragment of 857 bp was obtained (SEQ ID NO: 1). This cDNA fragment was designated as AtMVR gene, and the pGEM-T Easy vector containing AtMVR gene was designated as pAtMVR. The amino acid sequence encoded by the AtMVR gene is shown in SEQ ID NO: 2.

Example 2

Search for AtMVR Homologous Gene with Respect to AtMVR Gene

The search was made on databases having the entire nucleotide sequence of *Arabidopsis thaliana* based on the nucleotide sequence of the AtMVR gene and found that in addition to the nucleotide sequence of the AtMVR gene there are 13 AtMVR homologous genes on the *Arabidopsis thaliana* genome.

The respective AtMVR homologous genes were designated as AtMVR3-1 to AtMVR3-13. The nucleotide sequence of each of the AtMVR homologous genes and the putative amino acid sequence encoded by the relevant AtMVR homologous gene are shown by the SEQ ID NOs. listed in Table 9 below. Table 9 also lists the results of homology analysis between the AtMVR gene and each AtMVR homologous gene. The homology analysis was conducted using BLAST P at the amino acid level. The term "Identities" refers to 100% correspondence in terms of amino acids. Amino acids may be classified based on the chemical properties of their side chains. In the BLOSUM62 amino acid substitution matrix, amino acids are classified into: an amino acid with a mercapto group (C); hydrophilic amino acids that have low molecular weights (S, T, P, A, G); acidic amino acids (N, D, E, Q); basic amino acids (H, R, K); hydrophobic amino acids that have low molecular weights (M, I, L, V); and aromatic amino acids (F, Y, W). In Table 9, the term "Identities" refers to 100% correspondence in terms of amino acids and the term "Positives" refers to the numerical value when amino acids having a positive score in the BLOSUM 62 amino acid substitution matrix are added to those having 100% correspondence.

TABLE 9

| Name of AtMVR homologous gene | Nucleotide sequence | Amino acid sequence | Identities (%) | Positives (%) |
|---|---|---|---|---|
| AtMVR3-1 | SEQ ID NO: 4 | SEQ ID NO: 5 | 57 | 70 |
| AtMVR3-2 | SEQ ID NO: 6 | SEQ ID NO: 7 | 55 | 69 |
| AtMVR3-3 | SEQ ID NO: 8 | SEQ ID NO: 9 | 39 | 56 |
| AtMVR3-4 | SEQ ID NO: 10 | SEQ ID NO: 11 | 39 | 55 |
| AtMVR3-5 | SEQ ID NO: 12 | SEQ ID NO: 13 | 37 | 54 |
| AtMVR3-6 | SEQ ID NO: 14 | SEQ ID NO: 15 | 36 | 52 |
| AtMVR3-7 | SEQ ID NO: 16 | SEQ ID NO: 17 | 34 | 52 |
| AtMVR3-8 | SEQ ID NO: 18 | SEQ ID NO: 19 | 34 | 51 |
| AtMVR3-9 | SEQ ID NO: 20 | SEQ ID NO: 21 | 37 | 58 |
| AtMVR3-10 | SEQ ID NO: 22 | SEQ ID NO: 23 | 25 | 44 |
| AtMVR3-11 | SEQ ID NO: 24 | SEQ ID NO: 25 | 33* | 51* |
| AtMVR3-12 | SEQ ID NO: 26 | SEQ ID NO: 27 | 25 | 41 |
| AtMVR3-13 | SEQ ID NO: 28 | SEQ ID NO: 29 | 22 | 41 |

*The comparison with AtMVR3-11 shows the result of homology comparison with a partial sequence of AtMVR3-11.

As shown in Table 9, homology between AtMVR and the 13 AtMVR homologous genes ranged from 22 to 57% for Identities and from 41 to 70% for Positives.

Example 3

Construction of AtMVR Expression Vector for Plant and Production of AtMVR Transgenic Plant The transformation techniques applied herein were in accordance with a vector system described by Pellegrineschi et al. (Biochemical Society Transitions 23, 247-250, 1995) based on the *Agrobacterium* gene transport system outlined by Hinchee et al. (Plant Cell and Tissue Culture, pp. 231-270, Eds. I. K. Vasil, T. A Thorpe, Kluwer Academic Publisher, 1994).

(1) Construction of AtMVR Expression Vector for Plant

The AtMVR gene sequence was excised from pAtMVR using SacI/SacII and subcloned into pBlueScript (STRATAGENE). Subsequently, a fragment containing the AtMVR gene sequence was cleaved with XbaI/SacI and introduced at XbaI/SacI site that is present downstream of the CaMV 35S promoter of pBI121 (manufactured by Clontech). The resulting vector was used below as an AtMVR expression vector for plant.

(2) Production of AtMVR Transgenic Plant

The AtMVR expression vector for plant produced in the above (1) was introduced into *Agrobacterium tumefaciens* LBA4404 strain by the electroporation method (Plant Molecular Biology Manual, Second Edition, B. G. Stanton, A. S. Robbert, Kluwer Academic Publishers, 1994). Subsequently, the *Agrobacterium tumefaciens* having the AtMVR expression vector for plant introduced therein was introduced into wild-type *Arabidopsis thaliana* ecotype Col-0 by an infiltration method described by Clough et al. (The Plant Journal 16: 735-743, 1998).

Transformants were screened in a kanamycin-containing medium, and a T3 generation plant (homozygous line having 1 AtMVR gene introduced) was produced by self-pollination.

Next, the amount of the introduced AtMVR gene expressed was examined. Seeds of a transformant produced as described above and a non-transformant were respectively planted in pots containing vermiculite (Asahi Kagaku Kogyo Co., Ltd.) and allowed to grow for approximately one month under a light intensity of 100 µE/m²/s at 23° C. with a photoperiod condition of 16 hrs photoperiod/8 hrs dark period.

After growing, total RNA was extracted from the transformant and the wild-type *Arabidopsis thaliana* ecotype Col-0 non-transformant using the RNeasy Plant Mini Kit (QIAGEN). Thereafter, 1 µg of RNA was subjected to reverse transcription using the ProSTAR First Strand RT-PCR Kit (STRATAGEN). PCR was then performed using the following reaction mixture (Table 10) containing Takara EX-Taq (TAKARA BIO) employing 1/50 volume of the synthesized cDNA as a template and using primers for the AtMVR gene (primer 141d1 (SEQ ID NO: 38) and primer 141d2 (SEQ ID NO: 39)).

TABLE 10

| PCR reaction mixture: | |
|---|---|
| Template (cDNA): | 50 ng |
| 10x Ex Taq buffer (TAKARA BIO Inc.): | 2 µl |
| dNTPs: | 200 µM |
| Each primer: | 0.2 µM |
| Takara EX-Taq: | 1 unit |
| Total volume | 20 µl |

Thirty cycles of 94° C. (30 sec)/55° C. (30 sec)/72° C. (60 sec) were employed as the reaction conditions.

The amplification products were subjected to electrophoresis on agarose gel. FIG. 1 shows the results of electrophoresis. As can be seen from FIG. 1, in comparison to the non-transformant, the produced transformant overexpressed the AtMVR gene.

Example 4

Evaluation of Paraquat Resistance of AtMVR Gene Transformant

Figure 2:
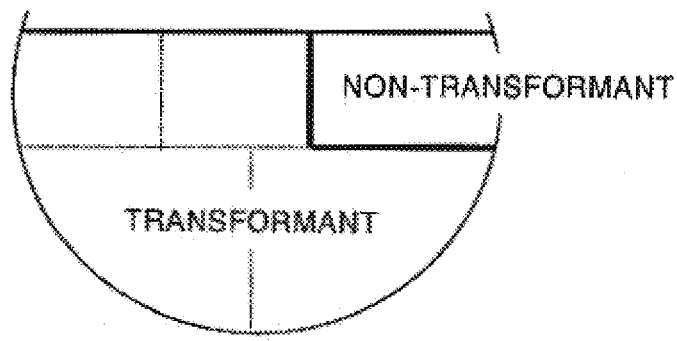
FIG. 2A is a schematic diagram showing the location of an AtMVR gene transformant and a non-transformant in FIGS. 2B and 2C.
FIG. 2B is a photograph showing the growth of an AtMVR gene transformant and a non-transformant in a ½ MS culture medium without paraquat.
FIG. 2C is a photograph showing the growth of an AtMVR gene transformant and a non-transformant in a ½ MS culture medium with paraquat.
Figure 2:
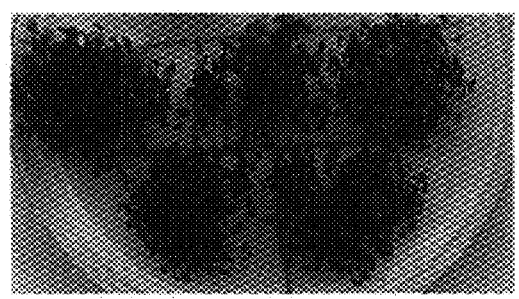
Figure 2:
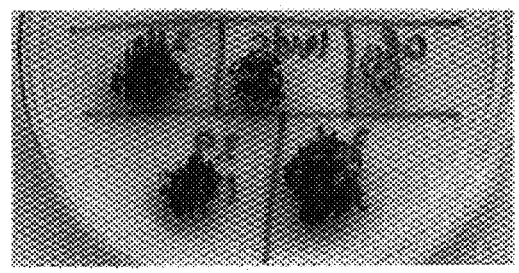

Seeds derived from the produced AtMVR gene transformant and non-transformant (wild-type *Arabidopsis thaliana* ecotype Col-0) were sterilely inoculated in ½ MS agar (1%) medium (2.3 µl of Murashige and Skoog Plant Salt Mixture (Wako Pure Chemical Industries Ltd.), 1.5 mg/l of thiamine hydrochloride, 2.5 mg/l of nicotinic acid, 0.25 mg/l of pyridoxine hydrochloride, 1.5% of sucrose) containing 3 µM of paraquat (methyl viologen (Sigma Chemical Co.)), and cultured for eight days at 22° C. under irradiation of light of 60 µmol/m²/s (cycle of 16 hrs photoperiod/8 hrs dark period). After culture, the growth of germinated individuals was evaluated. The results are shown in FIG. 2, wherein FIG. 2B is a photograph showing growth of an AtMVR gene transformant and a non-transformant in a ½ MS culture medium without paraquat, and FIG. 2C is a photograph showing growth of an AtMVR gene transformant and a non-transformant in a ½ MS culture medium with paraquat. FIG. 2A is a schematic diagram showing the location of the AtMVR gene transformant and the non-transformant in FIGS. 2B and 2C.

As can be seen from FIG. 2B, the results showed that in the culture medium without paraquat, the AtMVR gene transformant exhibited the same growth as the non-transformant. Meanwhile, as can be seen from FIG. 2C, in a medium containing paraquat the non-transformant developed chlorosis and died, i.e. growth was remarkably inhibited, while in contrast the seedling of the AtMVR gene transformant was able to grow. Thus, it was confirmed that in a medium without paraquat, the AtMVR gene transformant exhibited the same growth as a non-transformant regardless of expression of the AtMVR gene, and also that in a medium with paraquat, the AtMVR gene transformant had clearly greater paraquat resistance than the non-transformant.

Example 5

Isolation of Vascular Tissue/Trichome-specific Promoter

Seeds of *Arabidopsis thaliana* (*Arabidopsis thaliana* ecotype Columbia (Col-0)) were planted in pots containing vermiculite (Asahi Kagaku Kogyo Co., Ltd.) and allowed to grow for approximately one month under a light intensity of 100 µE/m$^2$/s at 23° C., under a photoperiod condition of 16 hrs photoperiod/8 hrs dark period.

After growing, genome DNA was prepared from leaves of individuals using DNeasy Plant Mini Kit (QIAGEN). Next, PCR was performed using the following reaction mixture (Table 11) containing Takara EX-Taq (TAKARA BIO Inc.) employing the obtained genome DNA as a template and using a primer 141dpF (SEQ ID NO: 40) and a primer 141dpR (SEQ ID NO: 41) based on the AtMVR gene fragment (SEQ ID NO: 35) described in above Example 1 under the reaction conditions described below.

TABLE 11

| | |
|---|---|
| Template genome DNA: | 50 ng |
| 10x Ex Taq buffer (TAKARA BIO Inc.): | 2 µl |
| dNTPs: | 200 µM |
| Each primer: | 0.2 µM |
| Takara EX-Taq: | 1 unit |
| Total volume: | 20 µl |

The reaction conditions were thirty cycles of 94° C. (30 sec)/55° C. (30 sec)/72° C. (60 sec).

The amplification product was cloned into pGEM-T Easy vector (Promega Corp.) and the nucleotide sequence was then determined using the ABI PRISM 310 genetic analyzer (Applied Biosystems). As a result, an AtMVR promoter of 1722 bp (SEQ ID NO: 3) was obtained.

Example 6

Analysis of Tissue Specificity of Vascular Tissue/Trichome-specific Promoter (1) Construction of Expression Vector Having AtMVR Promoter The AtMVR promoter was excised from the pGEM-T Easy vector having the AtMVR promoter (SEQ ID NO: 3) produced in Example 5 using HindIII/PstI and then subcloned into the upstream region of CaMV 35S promoter of pBI221 (Clontech). The resulting vector was treated with PstI/SmaI to remove the CaMV 35S promoter, and the ends were blunted using DNA T4 polymerase (TAKARA BIO Inc.) and allowed to self-ligate. As a result, the AtMVR promoter was ligated into the vector upstream of the β-Glucuronidase (GUS) gene. Subsequently, a fragment containing the AtMVR promoter and the GUS gene was excised from the above vector using HindIII/EcoRI, and then substituted for CaMV 35S promoter-β-GUS gene of pBI121 (Clontech). The vector thus obtained was employed as an expression vector having the AtMVR promoter for use below.

(2) Production of Transgenic Plant

In a similar manner to Example 3(2), the above expression vector having the AtMVR promoter was introduced into *Agrobacterium tumefaciens* LBA4404 strain, and this was then introduced into wild-type *Arabidopsis thaliana* ecotype Col-0 by the infiltration method. Thereafter, transformants were screened in a kanamycin-containing medium, and a T3 generation plant was produced by self-pollination.

(3) Analysis of Tissue Specificity of AtMVR Promoter

Seeds derived from the transformant produced in the above (2) were sterilely inoculated in ½ MS agar (1%) medium (2.3 g/l of Murashige and Skoog Plant Salt Mixture (Wako Pure Chemical Industries Ltd.), 1.5 mg/l of thiamine hydrochloride, 2.5 mg/l of nicotinic acid, 0.25 mg/l of pyridoxine hydrochloride, 1.5% of sucrose), and cultured at 22° C. under irradiation of light of 60 µE/m$^2$/s (cycle of 16 hrs photoperiod/8 hrs dark period) for approximately 7 days.

After culture, transformants that grew were fixed with acetone. A reaction mixture containing 5-brome-4-chloro-3-indolyl-β-D-glucuronide (X-Gluc) was added to the fixed tissue so as to immerse the entire tissue. The composition of the reaction mixture was: 1.9 mM of X-Gluc, 0.5 mM of $K_3Fe(CN)_6$, 0.5 mM of $K_4Fe(CN)_6$, and 0.3% of Triton X-100.

The container was then sealed and incubated overnight in a 37° C. incubator. Thereafter, 70% ethanol was added to the mixture to terminate the reaction, and coloring was observed. (Shokubutsu No Saibo Wo Miru Jikken Purotokoru (Protocols of Experiments for Observing Cells of Plants), Eds. Fukuda H., Nishimura M., & Nakamura K., (1997), pp 71-79, Shujunsha Co., Ltd., Tokyo). The results are shown in FIGS. 3 to 5, wherein FIGS. 3 to 5 are photomicrographs of an entire transformant, a leaf of a transformant, and a root of a transformant, respectively.

Figure 3:
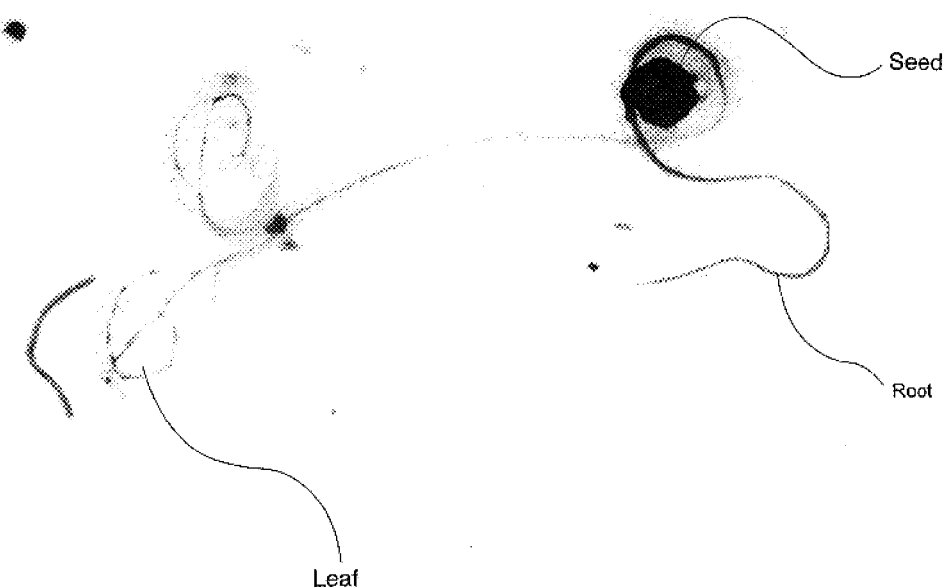
FIG. 3 is a photomicrograph of an entire transformant containing the GUS gene and an AtMVR promoter histochemically colored with GUS.
Figure 4:
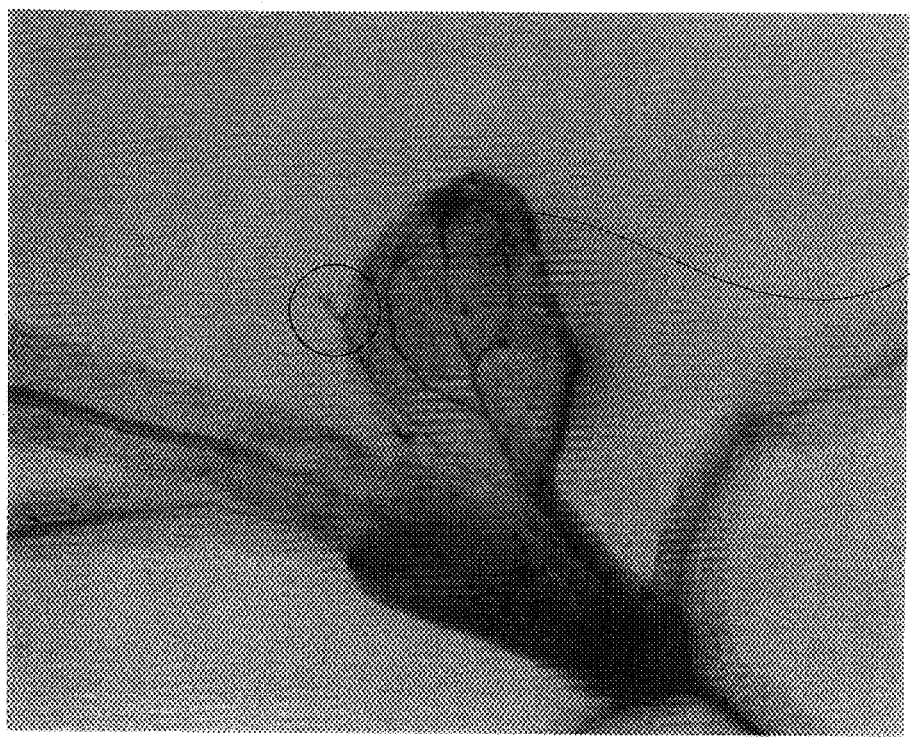
FIG. 4 is a photomicrograph of a leaf of a transformant containing the GUS gene and an AtMVR promoter histochemically colored with GUS.
Figure 5:
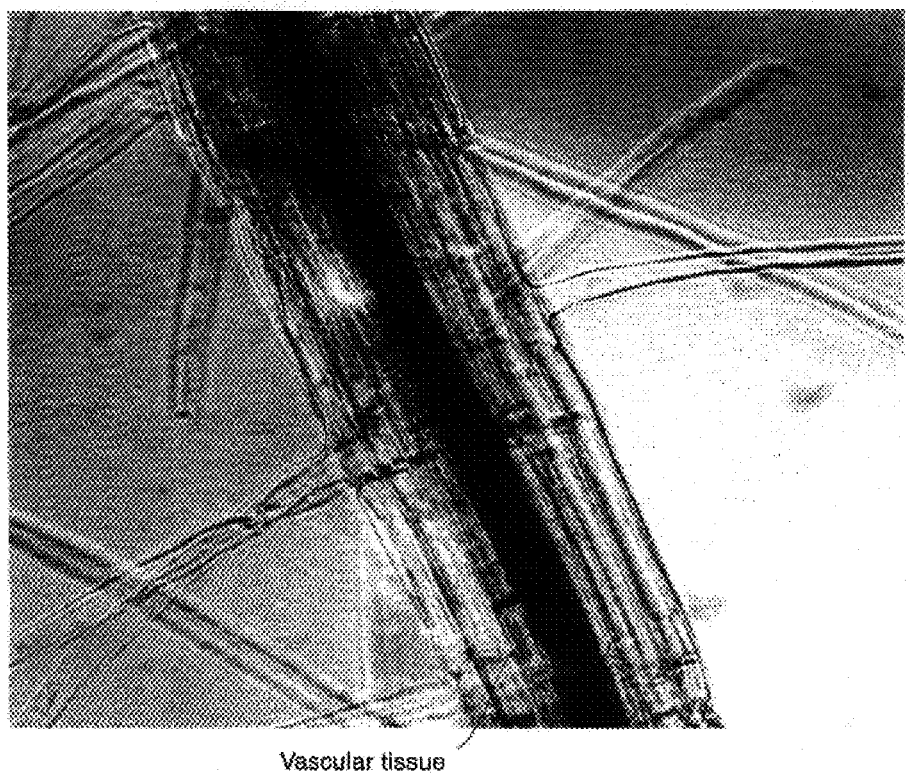
FIG. 5 is a photomicrograph of a root of a transformant containing the GUS gene and an AtMVR promoter histochemically colored with GUS.

As can be seen from FIGS. 3 to 5, specific coloring was observed in the vascular tissue and trichome. Thus, it was confirmed that the obtained AtMVR promoter (SEQ ID NO: 3) is a transcriptional promoter having tissue-specific transcriptional activity in a vascular tissue and trichome.

Free Text for Sequence Listing

SEQ ID NOS: 31 to 41 are primers.

In SEQ ID NO: 34, n represents a, g, c, or t (location: 1 and 11), s represents g or c (location: 7), and w represents a or t (location: 8 and 13).

In SEQ ID NO: 35, n represents a, g, c, or t (location: 13, 35, 73, 108, 156, 190, 198 and 201).

INDUSTRIAL APPLICABILITY

According to the present invention there is provided a paraquat resistance gene and a vascular tissue- and trichome-specific promoter. A paraquat resistance gene according to the present invention is capable of imparting resistance that is specific to paraquat without affecting growth regulation that undergoes control by the generation of active oxygens under various environments.

Further, the vascular tissue- and trichome-specific promoter according to the present invention enables the regulation of gene expression in a vascular tissue and trichome of a plant.

What is claimed is:

1. A method for screening for a transgenic plant, comprising introducing a recombinant vector into a plant, wherein the recombinant vector comprises a gene encoding a protein of the following (a) or (b):
   (a) a protein comprising the amino acid sequence represented by SEQ ID NO: 2;
   (b) a protein consisting of an amino acid sequence having a substitution, deletion or addition of one to ten amino acids relative to the amino acid sequence represented by SEQ ID NO: 2 and capable of imparting paraquat resistance;
   and wherein the recombinant vector further comprises a foreign gene or a foreign DNA fragment; and
screening for a transgenic plant on the basis of paraquat resistance as an indicator.

2. The method of claim 1, wherein the screening for a transgenic plant comprises growing the plant in a paraquat-containing medium.

3. The method of claim 2, wherein the paraquat in the paraquat-containing medium is present at a concentration of between 0.1 and 3.0 µM.

4. The method of claim 3, wherein the paraquat in the paraquat-containing medium is present at a concentration of 3.0 µM.

5. A method for imparting paraquat resistance to a plant, comprising introducing a recombinant vector into a plant, wherein the recombinant vector comprises a gene encoding a protein of the following (a) or (b):
   (a) a protein comprising the amino acid sequence represented by SEQ ID NO: 2;
   (b) a protein consisting of an amino acid sequence having a substitution, deletion or addition of one to ten amino acids relative to the amino acid sequence represented by SEQ ID NO: 2 and capable of imparting paraquat resistance;
imparting paraquat resistance; and
confirming paraquat resistance.

6. The method of claim 5, wherein paraquat resistance is confirmed by determining that the plant is capable of growing in the presence of paraquat.

7. The method of claim 6, wherein the paraquat is present in a culture medium.

8. The method of claim 7, wherein the paraquat is present at a concentration of between 0.1 and 3.0 µM.

9. The method of claim 8, wherein the paraquat is present at a concentration of 3.0 µM.

10. A method for screening for a transgenic plant, comprising introducing a recombinant vector into a plant, wherein the recombinant vector comprises a gene encoding a protein of the following (a) or (b):
   (a) a protein comprising the amino acid sequence represented by SEQ ID NO: 2;
   (b) a protein consisting of an amino acid sequence having a substitution, deletion or addition of one to ten amino acids relative to the amino acid sequence represented by SEQ ID NO: 2 and capable of imparting paraquat resistance; and
screening for a transgenic plant on the basis of paraquat resistance as an indicator.

11. The method of claim 10, wherein the screening for a transgenic plant comprises growing the plant in a paraquat-containing medium.

12. The method of claim 11, wherein the paraquat in the paraquat-containing medium is present at a concentration of between 0.1 and 3.0 µM.

13. The method of claim 12, wherein the paraquat in the paraquat-containing medium is present at a concentration of 3.0 µM.

14. The method of claim 1, 5, or 10, wherein the plant is selected from Poaceae, Brassicaceae, Solanaceae, and Leguminosae.

15. The method of claim 14, wherein the plant is a Brassicaceae, and the Brassicaceae is *Arabidopsis thaliana*.

* * * * *

SEQUENCE LISTING

<160> NUMBER OF SEQ ID NOS: 41

<210> SEQ ID NO 1
<211> LENGTH: 855
<212> TYPE: DNA
<213> ORGANISM: Arabidopsis thaliana

<400> SEQUENCE: 1

```
cttcttcaat catcaccatg gtacgtttta gtaacagtct tgtaggaata ctcaacttct      60
tcgtcttcct tctctcggtt cccatactct caaccggaat ctggctcagc cttaaagcca     120
cgacgcaatg cgagagattc ctcgacaaac ccatgatcgc tctcggtgtt ttcctcatga     180
taatcgcaat cgctggagtc gttggatctt gttgcagagt gacgtggctt ctctggtcct     240
atctctttgt gatgttcttc ttaatcctca tcgtcctctg tttcaccatc tttgccttcg     300
ttgtcactag taaaggctcc ggcgaaacta tccaaggaaa agcttataag gagtataggc     360
tcgaggctta ctctgattgg ttgcagaggc gtgtgaacaa cgctaagcat tggaacagca     420
ttagaagctg tctttatgag agcaagttct gttataactt ggagttagtc actgctaatc     480
acactgtttc tgatttctac aaagaagatc tcactgcttt tgagtctggt tgctgcaagc     540
cctctaatga ctgtgacttc acctacataa cttcaacaac ttggaataaa acatcaggaa     600
cacataaaaa ctcagattgc caactttggg acaacgaaaa gcataagctt tgctacaatt     660
gcaaagcctg caaggccggt tttctcgaca acctcaaggc cgcatggaaa agagttgcta     720
ttgtcaacat cattttcctt gtactcctcg ttgtcgtcta cgctatggga tgttgcgctt     780
tccgaaacaa caaagaagat agatatggcc gttccaatgg tttcaacaat tcttgatttg     840
cgccggttca agcta                                                      855
```

<210> SEQ ID NO 2
<211> LENGTH: 272
<212> TYPE: PRT
<213> ORGANISM: Arabidopsis thaliana

<400> SEQUENCE: 2

```
Met Val Arg Phe Ser Asn Ser Leu Val Gly Ile Leu Asn Phe Phe Val
  1               5                  10                  15

Phe Leu Leu Ser Val Pro Ile Leu Ser Thr Gly Ile Trp Leu Ser Leu
             20                  25                  30

Lys Ala Thr Thr Gln Cys Glu Arg Phe Leu Asp Lys Pro Met Ile Ala
         35                  40                  45

Leu Gly Val Phe Leu Met Ile Ile Ala Ile Ala Gly Val Val Gly Ser
     50                  55                  60

Cys Cys Arg Val Thr Trp Leu Leu Trp Ser Tyr Leu Phe Val Met Phe
 65                  70                  75                  80

Phe Leu Ile Leu Ile Val Leu Cys Phe Thr Ile Phe Ala Phe Val Val
                 85                  90                  95

Thr Ser Lys Gly Ser Gly Glu Thr Ile Gln Gly Lys Ala Tyr Lys Glu
            100                 105                 110

Tyr Arg Leu Glu Ala Tyr Ser Asp Trp Leu Gln Arg Arg Val Asn Asn
        115                 120                 125
```

```
Ala Lys His Trp Asn Ser Ile Arg Ser Cys Leu Tyr Glu Ser Lys Phe
    130                 135                 140
Cys Tyr Asn Leu Glu Leu Val Thr Ala Asn His Thr Val Ser Asp Phe
145                 150                 155                 160
Tyr Lys Glu Asp Leu Thr Ala Phe Glu Ser Gly Cys Cys Lys Pro Ser
                165                 170                 175
Asn Asp Cys Asp Phe Thr Tyr Ile Thr Ser Thr Trp Asn Lys Thr
            180                 185                 190
Ser Gly Thr His Lys Asn Ser Asp Cys Gln Leu Trp Asp Asn Glu Lys
        195                 200                 205
His Lys Leu Cys Tyr Asn Cys Lys Ala Cys Lys Ala Gly Phe Leu Asp
    210                 215                 220
Asn Leu Lys Ala Ala Trp Lys Arg Val Ala Ile Val Asn Ile Ile Phe
225                 230                 235                 240
Leu Val Leu Leu Val Val Val Tyr Ala Met Gly Cys Cys Ala Phe Arg
                245                 250                 255
Asn Asn Lys Glu Asp Arg Tyr Gly Arg Ser Asn Gly Phe Asn Asn Ser
                260                 265                 270
```

<210> SEQ ID NO 3
<211> LENGTH: 1722
<212> TYPE: DNA
<213> ORGANISM: Arabidopsis thaliana

<400> SEQUENCE: 3

| | | |
|---|---|---|
| agccaagctt gtacattaac cgtgactatt attattattt ttaatgaaat tatttttttc | 60 |
| tttctcccat acatttata tgattcgttt cttttaggat tattataaaa tctaaatgat | 120 |
| tcgtttctct aagacaagc aaaaaccgaa aaaggacag cctattatac cgcgttaatt | 180 |
| taaagttaat cgtgattgtg ttaatcttga aatgtatttg aacattttg ttttcttaat | 240 |
| acagaattga ttgatgtaag gcagcaaata ttttcctacc aaaataattt gttagggatc | 300 |
| ttttagaaaa agaaataaaa taaaaaaaag ggataagga cagctgggaa gagtgggaca | 360 |
| gcagagaaag tggtggtgta cggtaaccgt tggatccgat gaggaattta ataaaggtag | 420 |
| tcgtaatctt acggtccagc tgtgaagtac tcatgccacg ttatcttctc caccgacagt | 480 |
| acattgttac tatagcagct atagtatagc ctattcaatc atttgtattt taatggtaag | 540 |
| caaagaggaa actatgtaga agtttcttat cttatagttt ctcaagtctt ttagttttgg | 600 |
| ttccataatc cttttttag tatgtgaagg tgaaggtgag tttagtatgt gattttagt | 660 |
| atgatttggt tgataacgtt ttcactcgac taattatata cttcagaagg atagtaatag | 720 |
| aataccaaaa taattaaatg attggttagt gccttagtgg agactttta accgattcta | 780 |
| atagactaat gatgtagcta agcatttatt tgggatcatc actgtttgaa aacgtgaaat | 840 |
| gtgataaaag ttatgaaacg attaaaatat aaaataaccg tacaaaacat tatgtaccgt | 900 |
| ttttttctct gttcttttgg cgatttggtt tagttcgtta cactctaaat gttattgcag | 960 |
| atatatatat aatgatgcat ttgcatctga ggaacatata attccggtta acacttccaa | 1020 |
| atcttatatc cgtctaggta gggattttat aaatcatttg tgtcatcatg cgttatgctt | 1080 |
| gtcggctttg accataacgc agagatatag aactagcttt tacttaactt ttagatttat | 1140 |
| tatttgatct agagttaagt ggagatatat agtgttttg ttagattatt ggtggatgtg | 1200 |
| agagtttgtc tttagtttca agttgagaat ataaggcaag aggagactct gaggcaatca | 1260 |
| gaggttttga ttggcaaaat atccaaaagg cccaaaccaa gtcgaagccc atctcgtaca | 1320 |

```
aaaaaagaaa gagatctgta agaaaaaata ttctttgata ttcttacaaa aataagtgta     1380 aaactttat  tagtcaaaat cttcaatctt taaaaactct catcactcct acgaaagcgc     1440
gtgagagtta tgagacattc cttaatagca ttactcacaa gtcacaagtt caaaacgtct    1500
gactgaaaca gaaacaagcc tttgttgaag tcttgaagaa gagacattag tactcgtcgt    1560
atagccataa aaggtaatat acgaaatttc ttcgctaatc tcttcacctt cctctacgcg    1620
tttcactttc actttataaa tccaaatctc ccttcgaaaa cataatcaca caaatcccct    1680
ttttggtttc tccaaatctt caaatcttct tcaatcatca cc                       1722
```

<210> SEQ ID NO 4
<211> LENGTH: 822
<212> TYPE: DNA
<213> ORGANISM: Arabidopsis thaliana

<400> SEQUENCE: 4

```
atggctcgtt gtagcaacaa tctcgtaggg atactcaatt tcctagtatt tcttctctcg     60
atcccaatct tagctggtgg aatctggcta agccaaaaag ggtcaacaga gtgtgaaaga    120
ttcctagaca aaccagtgat tgctcttggt gttttcctta tggttgtagc aatagctggt    180
ctaataggtt catgttgtag agtcacatgg cttcttggg tttatctctt tgtcatgttc     240
cttttgattc tccttgtgtt ctgtataaca gttttgcct ttgttgttac taacaaagga    300
gctggtgaag ctattgaagg aaaaggttat aaagagtata acttggtga ttactctact     360 tggttacaga aacgtgttga gaatggtaaa aattggaata agattaggag ttgtcttgtg    420
gagagcaaag tttgttctaa gcttgaagcc aagtttgtta atgttcctgt caatagtttc    480
tacaaggaac atcttactgc tcttcagtct ggttgctgca aaccttcaga tgaatgtggt    540
ttcgagtacg taaacccaac aacctggacc aagaacacaa cgggaacaca cactaatcca    600
gactgccaaa cctgggacaa cgcaaaagaa aagctctgct tcgattgtca atcttgtaaa    660
gcgggtctac tcgacaacgt caaaagcgct tggaagaaag ttgcaatcgt taacatcgtc    720
ttccttgtct tcctcatcat tgtctactct gttggttgct gtgctttcag gaacaacaag    780
agggatgaca gttattcccg tacctacgga tataagcctt ga                       822
```

<210> SEQ ID NO 5
<211> LENGTH: 272
<212> TYPE: PRT
<213> ORGANISM: Arabidopsis thaliana

<400> SEQUENCE: 5

```
Met Ala Arg Cys Ser Asn Asn Leu Val Gly Ile Leu Asn Phe Leu Val
  1               5                  10                  15

Phe Leu Leu Ser Ile Pro Ile Leu Ala Gly Gly Ile Trp Leu Ser Gln
             20                  25                  30

Lys Gly Ser Thr Glu Cys Glu Arg Phe Leu Asp Lys Pro Val Ile Ala
         35                  40                  45

Leu Gly Val Phe Leu Met Val Val Ala Ile Ala Gly Leu Ile Gly Ser
     50                  55                  60

Cys Cys Arg Val Thr Trp Leu Leu Trp Val Tyr Leu Phe Val Met Phe
 65                  70                  75                  80

Leu Leu Ile Leu Leu Val Phe Cys Ile Thr Val Phe Ala Phe Val Val
                 85                  90                  95

Thr Asn Lys Gly Ala Gly Glu Ala Ile Glu Gly Lys Gly Tyr Lys Glu
            100                 105                 110
```

Tyr Lys Leu Gly Asp Tyr Ser Thr Leu Gln Lys Arg Val Glu Asn Gly
            115                 120                 125

Lys Asn Trp Asn Lys Ile Arg Ser Cys Leu Val Glu Ser Lys Val Cys
130                 135                 140

Ser Lys Leu Glu Ala Lys Phe Val Asn Val Pro Val Asn Ser Phe Tyr
145                 150                 155                 160

Lys Glu His Leu Thr Ala Leu Gln Ser Gly Cys Cys Lys Pro Ser Asp
            165                 170                 175

Glu Cys Gly Phe Glu Tyr Val Asn Pro Thr Thr Trp Thr Lys Asn Thr
            180                 185                 190

Thr Gly Thr His Thr Asn Pro Asp Cys Gln Thr Trp Asp Asn Ala Lys
            195                 200                 205

Glu Lys Leu Cys Phe Asp Cys Gln Ser Cys Lys Ala Gly Leu Leu Asp
            210                 215                 220

Asn Val Lys Ser Ala Trp Lys Lys Val Ala Ile Val Asn Ile Val Phe
225                 230                 235                 240

Leu Val Phe Leu Ile Ile Val Tyr Ser Val Gly Cys Cys Ala Phe Arg
            245                 250                 255

Asn Asn Lys Arg Asp Asp Ser Tyr Ser Arg Thr Tyr Gly Tyr Lys Pro
            260                 265                 270

<210> SEQ ID NO 6
<211> LENGTH: 792
<212> TYPE: DNA
<213> ORGANISM: Arabidopsis thaliana

<400> SEQUENCE: 6
atggttcagt gtagcaacaa tctcctcgga atcctcaatt tcttcacatt cctcctctca     60
atcccaattc tctccgccgg gatctggctc ggcaaaaatg cagcaaccga atgcgaacgt    120
ttcctcgaca aaccaatggt cgtactcgga atcttcctca tgttcgtctc aatcgccgga    180
ctcgtcggtg cttgttgccg tgtctcttgc ctcctctggc tttacctctt cgctatgttc    240
ctcctcattc tcctcggctt ctgtttcaca atcttcgctt cgcagtcac aaaccgcggc     300 gccggtgagg ttatatcgga tcgagggtat aaagagtatc atgtcgccga ttactctaat    360
tggttgcaga aacgtgtcaa caatgctaag aattgggaac ggatcaggag ttgtttgatg    420
tactctgacg tttgctccac ttatcgtact cgttatgcca gcattaacgt tgaagatttc    480
tacaaatcta atcttaatgc tcttcagtct ggttgttgta agccgtccaa tgactgtaac    540
ttcacctatg tgaacccgac tacttggaca agactcctg gtccatacaa aaacgaggac     600
tgtaatgtgt gggacaacaa accaggaact ctctgctacg actgtgaagc ctgcaaggct    660
ggtctgcttg acaacatcaa gaactcatgg aaaaaggtgg ctaaggtcaa cattgtcttc    720
ctcatattcc tcattatcgt ctactctgtt ggttgttgtg cgttcaggaa caacaggaaa    780
cgcagttggt aa                                                        792

<210> SEQ ID NO 7
<211> LENGTH: 263
<212> TYPE: PRT
<213> ORGANISM: Arabidopsis thaliana

<400> SEQUENCE: 7

Met Val Gln Cys Ser Asn Asn Leu Leu Gly Ile Leu Asn Phe Phe Thr
 1               5                  10                  15

Phe Leu Leu Ser Ile Pro Ile Leu Ser Ala Gly Ile Trp Leu Gly Lys
            20                  25                  30

```
Asn Ala Ala Thr Glu Cys Glu Arg Phe Leu Asp Lys Pro Met Val Val
             35                  40                  45

Leu Gly Ile Phe Leu Met Phe Val Ser Ile Ala Gly Leu Val Gly Ala
 50                  55                  60

Cys Cys Arg Val Ser Cys Leu Leu Trp Leu Tyr Leu Phe Ala Met Phe
 65                  70                  75                  80

Leu Leu Ile Leu Leu Gly Phe Cys Phe Thr Ile Phe Ala Phe Ala Val
                 85                  90                  95

Thr Asn Arg Gly Ala Gly Glu Val Ile Ser Asp Arg Gly Tyr Lys Glu
                100                 105                 110

Tyr His Val Ala Asp Tyr Ser Asn Trp Leu Gln Lys Arg Val Asn Asn
            115                 120                 125

Ala Lys Asn Trp Glu Arg Ile Arg Ser Cys Leu Met Tyr Ser Asp Val
130                 135                 140

Cys Ser Thr Tyr Arg Thr Arg Tyr Ala Ser Ile Asn Val Glu Asp Phe
145                 150                 155                 160

Tyr Lys Ser Asn Leu Asn Ala Leu Gln Ser Gly Cys Cys Lys Pro Ser
                165                 170                 175

Asn Asp Cys Asn Phe Thr Tyr Val Asn Pro Thr Thr Trp Thr Lys Thr
            180                 185                 190

Pro Gly Pro Tyr Lys Asn Glu Asp Cys Asn Val Trp Asp Asn Lys Pro
        195                 200                 205

Gly Thr Leu Cys Tyr Asp Cys Glu Ala Cys Lys Ala Gly Leu Leu Asp
    210                 215                 220

Asn Ile Lys Asn Ser Trp Lys Lys Val Ala Lys Val Asn Ile Val Phe
225                 230                 235                 240

Leu Ile Phe Leu Ile Ile Val Tyr Ser Val Gly Cys Cys Ala Phe Arg
                245                 250                 255

Asn Asn Arg Lys Arg Ser Trp
            260
```

```
<210> SEQ ID NO 8
<211> LENGTH: 984
<212> TYPE: DNA
<213> ORGANISM: Arabidopsis thaliana

<400> SEQUENCE: 8
atgagatcga gaagtaacct tataggtctc ataaacttct tcactttcct cctgtcgatt      60
cctatcctcg gcggtggaat atggcttagc agccgagcta actcaaccga ttgcctcaga     120
ttcctccagt ggccactcat tatcatcgga atatcaatca tggtcatatc tttagccgga     180
atcgccggag cttgttacca aaacaagttc tcatgtggc tttaccttt caccatgttc      240
tttgtaatcg ctgctcttat aggattcaca atcttcgctt acgtagttac tgataaaggc     300
tcaggccggt ttgtgatgaa ccgtcggtat cttgattatt atctcaatga ttattccggt     360
tggttaaagg accgtgtcac agataatgga tattggagag atatcggatc gtgtgttaga     420
gattctggag tttgtaagaa gattggaaga gatttaaatg gtgttccaga aactgctcat     480
atgttttact tcagaaatct ttctcctgtt gagtccggat gttgcaagcc gccaacagat     540
tgtggctata cgtacgtgaa cgagacagtg tggattccgg aggagaaat ggtgggaccg      600
aaccccggact gtatgttgtg aacaatgac cagagactac tctgttacca atgcagctct     660
tgtaaagccg gtgttcttgg tagcttgaaa aagagttgga aaaagtctc ggtgatcaac      720
atcgtggttg tgatcatact tgttatcttc tatgtcatcg cgtgtgcggc ttaccagaat     780
```

```
gttaagagga tgtataatga cgaaccggtc ggtgaggcta ggatgaccaa tctcatccta    840
gtcattttca aatttaagga gattttggta cagttttcct tcggaattgt gttttatta     900 ctctttaatg gtttaatggt ctgttgttgt aatgataaat ttgcttttag tgttttcttc    960
tttggatatg ttacatatgc atga                                           984
```

<210> SEQ ID NO 9
<211> LENGTH: 327
<212> TYPE: PRT
<213> ORGANISM: Arabidopsis thaliana

<400> SEQUENCE: 9

```
Met Arg Ser Arg Ser Asn Leu Ile Gly Leu Ile Asn Phe Phe Thr Phe
  1               5                  10                  15

Leu Leu Ser Ile Pro Ile Leu Gly Gly Gly Ile Trp Leu Ser Ser Arg
             20                  25                  30

Ala Asn Ser Thr Asp Cys Leu Arg Phe Leu Gln Trp Pro Leu Ile Ile
         35                  40                  45

Ile Gly Ile Ser Ile Met Val Ile Ser Leu Ala Gly Ile Ala Gly Ala
     50                  55                  60

Cys Tyr Gln Asn Lys Phe Leu Met Trp Leu Tyr Leu Phe Thr Met Phe
 65                  70                  75                  80

Phe Val Ile Ala Ala Leu Ile Gly Phe Thr Ile Phe Ala Tyr Val Val
                 85                  90                  95

Thr Asp Lys Gly Ser Gly Arg Phe Val Met Asn Arg Arg Tyr Leu Asp
            100                 105                 110

Tyr Tyr Leu Asn Asp Tyr Ser Gly Trp Leu Lys Asp Arg Val Thr Asp
        115                 120                 125

Asn Gly Tyr Trp Arg Asp Ile Gly Ser Cys Val Arg Asp Ser Gly Val
    130                 135                 140

Cys Lys Lys Ile Gly Arg Asp Leu Asn Gly Val Pro Glu Thr Ala His
145                 150                 155                 160

Met Phe Tyr Phe Arg Asn Leu Ser Pro Val Glu Ser Gly Cys Cys Lys
                165                 170                 175

Pro Pro Thr Asp Cys Gly Tyr Thr Tyr Val Asn Glu Thr Val Trp Ile
            180                 185                 190

Pro Gly Gly Glu Met Val Gly Pro Asn Pro Asp Cys Met Leu Trp Asn
        195                 200                 205

Asn Asp Gln Arg Leu Leu Cys Tyr Gln Cys Ser Ser Cys Lys Ala Gly
    210                 215                 220

Val Leu Gly Ser Leu Lys Lys Ser Trp Arg Lys Val Ser Val Ile Asn
225                 230                 235                 240

Ile Val Val Val Ile Ile Leu Val Ile Phe Tyr Val Ile Ala Cys Ala
                245                 250                 255

Ala Tyr Gln Asn Val Lys Arg Met Tyr Asn Asp Glu Pro Val Gly Glu
            260                 265                 270

Ala Arg Met Thr Asn Leu Ile Leu Val Ile Phe Lys Phe Lys Glu Ile
        275                 280                 285

Leu Val Gln Phe Phe Gly Ile Val Phe Leu Leu Phe Asn Gly
    290                 295                 300

Leu Met Val Cys Cys Cys Asn Asp Lys Phe Ala Phe Ser Val Phe Phe
305                 310                 315                 320

Phe Gly Tyr Val Thr Tyr Ala
                325
```

<210> SEQ ID NO 10
<211> LENGTH: 858
<212> TYPE: DNA
<213> ORGANISM: Arabidopsis thaliana

<400> SEQUENCE: 10

| | | | | | |
|---|---|---|---|---|---|
| atgagaacaa | gcaaccatct | cataggttta | gtcaacttcc | tcactttcct | cctctcaata | 60 |
| ccaatcctcg | gcggtggaat | atggttaagc | agccgagcta | actccaccga | ctgtttaaga | 120 |
| ttccttcaat | ggcctctcat | cgtcatcgga | atctcaatca | tggtcgtatc | tttagctgga | 180 |
| ttcgctggag | cttgttaccg | taacaagttc | cttatgtggc | tatacctagt | agtcatgctt | 240 |
| ctcatcatcg | ctgctcttat | cggtttcatc | atcttcgctt | acgcggttac | agataaagga | 300 |
| tccggtcgaa | ccgtacttaa | ccggggttat | cttgactatt | atcttgaaga | ttactctggt | 360 |
| tggttgaaag | atcgagtttc | tgatgatagc | tattggggta | aaattagttc | ttgtcttaga | 420 |
| gattctggtg | cttgtagaaa | gattggaaga | aattttaatg | gtgtacctga | aactgctgat | 480 |
| atgttcttcc | ttagaagact | tagccctgtt | gagtccggtt | gttgcaagcc | accaacagat | 540 |
| tgcggttttt | catatgtgaa | tgagaccgga | tgggacacga | gaggagggat | gataggaccg | 600 |
| aaccaggact | gtatggtgtg | gagcaacgac | cagagcatgc | tctgttatca | gtgtagttct | 660 |
| tgtaaagctg | gtgttcttgg | gagtttgaag | aagagttgga | gaaaagtatc | ggtgatcaac | 720 |
| attgtggtac | ttatcattct | agttatcttt | tacgttatcg | cttatgcagc | ttataggaat | 780 |
| gtcaagagga | tcgataacga | tgaaccggct | ggtgaagcta | ggatgacaaa | atcacatcct | 840 |
| agtcatttcc | atctttga | | | | | 858 |

<210> SEQ ID NO 11
<211> LENGTH: 285
<212> TYPE: PRT
<213> ORGANISM: Arabidopsis thaliana

<400> SEQUENCE: 11

Met Arg Thr Ser Asn His Leu Ile Gly Leu Val Asn Phe Leu Thr Phe
1               5                   10                  15

Leu Leu Ser Ile Pro Ile Leu Gly Gly Gly Ile Trp Leu Ser Ser Arg
            20                  25                  30

Ala Asn Ser Thr Asp Cys Leu Arg Phe Leu Gln Trp Pro Leu Ile Val
        35                  40                  45

Ile Gly Ile Ser Ile Met Val Val Ser Leu Ala Gly Phe Ala Gly Ala
    50                  55                  60

Cys Tyr Arg Asn Lys Phe Leu Met Trp Leu Tyr Leu Val Val Met Leu
65                  70                  75                  80

Leu Ile Ile Ala Ala Leu Ile Gly Phe Ile Ile Phe Ala Tyr Ala Val
                85                  90                  95

Thr Asp Lys Gly Ser Gly Arg Thr Val Leu Asn Arg Gly Tyr Leu Asp
            100                 105                 110

Tyr Tyr Leu Glu Asp Tyr Ser Gly Trp Leu Lys Asp Arg Val Ser Asp
        115                 120                 125

Asp Ser Tyr Trp Gly Lys Ile Ser Ser Cys Leu Arg Asp Ser Gly Ala
    130                 135                 140

Cys Arg Lys Ile Gly Arg Asn Phe Asn Gly Val Pro Glu Thr Ala Asp
145                 150                 155                 160

Met Phe Phe Leu Arg Arg Leu Ser Pro Val Glu Ser Gly Cys Cys Lys
                165                 170                 175

```
Pro Pro Thr Asp Cys Gly Phe Ser Tyr Val Asn Glu Thr Gly Trp Asp
            180                 185                 190

Thr Arg Gly Gly Met Ile Gly Pro Asn Gln Asp Cys Met Val Trp Ser
        195                 200                 205

Asn Asp Gln Ser Met Leu Cys Tyr Gln Cys Ser Cys Lys Ala Gly
        210                 215                 220

Val Leu Gly Ser Leu Lys Lys Ser Trp Arg Lys Val Ser Val Ile Asn
225                 230                 235                 240

Ile Val Val Leu Ile Ile Leu Val Ile Phe Tyr Val Ile Ala Tyr Ala
                245                 250                 255

Ala Tyr Arg Asn Val Lys Arg Ile Asp Asn Asp Glu Pro Ala Gly Glu
            260                 265                 270

Ala Arg Met Thr Lys Ser His Pro Ser His Phe His Leu
            275                 280                 285

<210> SEQ ID NO 12
<211> LENGTH: 849
<212> TYPE: DNA
<213> ORGANISM: Arabidopsis thaliana

<400> SEQUENCE: 12
atgtacagat tcagcaacac agttattggg gtcttaaacc ttctcacctt actagcctcg      60
attccaatca tcggaaccgc tttatacaag gcaagaagca gcacgacatg tgaaaacttc    120
ctccagacgc cgctacttgt tataggattc atcatactca tagtttccct tgcgggattc    180
ataggagcct gcttcaacgt ggcatgggct ctttgggtgt acttagtggt catgatcttc    240
ctcatcgcta ccctaatggg tctaacgcta tttggtctgg tggtgacgag ccaaggaggt    300
ggagtggaag tgccagggag gatttataaa gagtataggc ttggagacta tcatccatgg    360
ttgagagaga gagttaggga tcctgagtat tggaactcca ttagaagctg tatcttgagt    420
tccaagactt gtactaagat tgagtcttgg actacacttg attatttcca aagagacatg    480
acttctgttc agtcgggatg ttgtaagcca ccgacggcgt gtacgtacga agctggagta    540
gtggacggag gaggagattg cttcagatgg aacaatggag tggagatgtt atgctacgag    600
tgcgatgctt gcaaggctgg tgttctcgaa gagatccgtc tcgactggag aaagttatcg    660
gttgtcaaca ttctcgtcct cgtcctcctc atcgcggtct acgccgctgg ttgctgcgcc    720
ttccacaaca ctcgccacgc agctcatcct taccatccat ctgatgataa ccgcatgacc    780
agagtccgtc ctcgttggga ctattactgg tggagatggt ggcacgaaaa gaaagagcag    840
ctttactaa                                                            849

<210> SEQ ID NO 13
<211> LENGTH: 282
<212> TYPE: PRT
<213> ORGANISM: Arabidopsis thaliana

<400> SEQUENCE: 13

Met Tyr Arg Phe Ser Asn Thr Val Ile Gly Val Leu Asn Leu Leu Thr
  1               5                  10                  15

Leu Leu Ala Ser Ile Pro Ile Ile Gly Thr Ala Leu Tyr Lys Ala Arg
             20                  25                  30

Ser Ser Thr Thr Cys Glu Asn Phe Leu Gln Thr Pro Leu Leu Val Ile
         35                  40                  45

Gly Phe Ile Ile Leu Ile Val Ser Leu Ala Gly Phe Ile Gly Ala Cys
     50                  55                  60
```

Phe Asn Val Ala Trp Ala Leu Trp Val Tyr Leu Val Met Ile Phe
 65                  70                  75                  80

Leu Ile Ala Thr Leu Met Gly Leu Thr Leu Phe Gly Leu Val Val Thr
             85                  90                  95

Ser Gln Gly Gly Gly Val Glu Val Pro Gly Arg Ile Tyr Lys Glu Tyr
            100                 105                 110

Arg Leu Gly Asp Tyr His Pro Trp Leu Arg Glu Arg Val Arg Asp Pro
        115                 120                 125

Glu Tyr Trp Asn Ser Ile Arg Ser Cys Ile Leu Ser Ser Lys Thr Cys
    130                 135                 140

Thr Lys Ile Glu Ser Trp Thr Thr Leu Asp Tyr Phe Gln Arg Asp Met
145                 150                 155                 160

Thr Ser Val Gln Ser Gly Cys Cys Lys Pro Pro Thr Ala Cys Thr Tyr
                165                 170                 175

Glu Ala Gly Val Val Asp Gly Gly Asp Cys Phe Arg Trp Asn Asn
            180                 185                 190

Gly Val Glu Met Leu Cys Tyr Glu Cys Asp Ala Cys Lys Ala Gly Val
        195                 200                 205

Leu Glu Glu Ile Arg Leu Asp Trp Arg Lys Leu Ser Val Val Asn Ile
    210                 215                 220

Leu Val Leu Val Leu Leu Ile Ala Val Tyr Ala Ala Gly Cys Cys Ala
225                 230                 235                 240

Phe His Asn Thr Arg His Ala Ala His Pro Tyr His Pro Ser Asp Asp
                245                 250                 255

Asn Arg Met Thr Arg Val Arg Pro Arg Trp Asp Tyr Tyr Trp Trp Arg
            260                 265                 270

Trp Trp His Glu Lys Lys Glu Gln Leu Tyr
        275                 280

<210> SEQ ID NO 14
<211> LENGTH: 810
<212> TYPE: DNA
<213> ORGANISM: Arabidopsis thaliana

<400> SEQUENCE: 14
atgcctttaa gcaacaatgt aattggttgc ataaacttca tcaccgtcct cctctccatt      60
ccggtcatcg cgccggaat ctggctagcc ataggaacag taaactcatg cgtcaagctt     120
cttcaatggc cagtaataat cctcggagtc ttaatcctct tagtgggtct cgctggtttc     180
attggagggt tttggagaat cacatggctt cttgttgttt acttaatcgc catgcttatt     240
ctcattgtac ttttgggttg ccttgtcgga tttatttaca tggttaccat aagaggctct     300
ggtcatccag aaccaagtag agcttatctt gagtatagtc ttcaagattt ctctggttgg     360
ttacgtagaa gagttcagag atcttataaa tgggaaagga tcgtacttg tttgagtaca     420 actaccattt gccctgaact aaatcagaga tacactttgg ctcaagattt cttcaatgct     480
catcttgatc ccattcaatc tggttgctgc aagcccccaa caaaatgtgg attcacattt     540
gttaatccta cttattggat aagtcccata gatatgtctg ctgatatgga ttgtctaaat     600
tggagcaatg accaaaacac tttgtgttac acttgtgatt cttgtaaagc cggcttgctc     660
gcaaatatta aggtagattg gttaaaagcg gatatcttc tactcttggc gcttatcgga     720
ttgattatcg tctacattat cgggtgctgc gcattccgta atgcgaaaac tgaggatatt     780
ttcaggaagt acaagcaggg ttatacttga                                      810

<210> SEQ ID NO 15
<211> LENGTH: 269
<212> TYPE: PRT
<213> ORGANISM: Arabidopsis thaliana

<400> SEQUENCE: 15

Met Pro Leu Ser Asn Asn Val Ile Gly Cys Ile Asn Phe Ile Thr Val
1               5                   10                  15

Leu Leu Ser Ile Pro Val Ile Gly Ala Gly Ile Trp Leu Ala Ile Gly
            20                  25                  30

Thr Val Asn Ser Cys Val Lys Leu Leu Gln Trp Pro Val Ile Ile Leu
        35                  40                  45

Gly Val Leu Ile Leu Leu Val Gly Leu Ala Gly Phe Ile Gly Gly Phe
    50                  55                  60

Trp Arg Ile Thr Trp Leu Leu Val Val Tyr Leu Ile Ala Met Leu Ile
65                  70                  75                  80

Leu Ile Val Leu Leu Gly Cys Leu Val Gly Phe Ile Tyr Met Val Thr
                85                  90                  95

Ile Arg Gly Ser Gly His Pro Glu Pro Ser Arg Ala Tyr Leu Glu Tyr
            100                 105                 110

Ser Leu Gln Asp Phe Ser Gly Trp Leu Arg Arg Val Gln Arg Ser
        115                 120                 125

Tyr Lys Trp Glu Arg Ile Arg Thr Cys Leu Ser Thr Thr Thr Ile Cys
    130                 135                 140

Pro Glu Leu Asn Gln Arg Tyr Thr Leu Ala Gln Asp Phe Phe Asn Ala
145                 150                 155                 160

His Leu Asp Pro Ile Gln Ser Gly Cys Cys Lys Pro Pro Thr Lys Cys
                165                 170                 175

Gly Phe Thr Phe Val Asn Pro Thr Tyr Trp Ile Ser Pro Ile Asp Met
            180                 185                 190

Ser Ala Asp Met Asp Cys Leu Asn Trp Ser Asn Asp Gln Asn Thr Leu
        195                 200                 205

Cys Tyr Thr Cys Asp Ser Cys Lys Ala Gly Leu Leu Ala Asn Ile Lys
    210                 215                 220

Val Asp Trp Leu Lys Ala Asp Ile Phe Leu Leu Ala Leu Ile Gly
225                 230                 235                 240

Leu Ile Ile Val Tyr Ile Ile Gly Cys Cys Ala Phe Arg Asn Ala Glu
                245                 250                 255

Thr Glu Asp Ile Phe Arg Lys Tyr Lys Gln Gly Tyr Thr
            260                 265

<210> SEQ ID NO 16
<211> LENGTH: 813
<212> TYPE: DNA
<213> ORGANISM: Arabidopsis thaliana

<400> SEQUENCE: 16
atggcgttag cgaataactt aacggcgata ctcaacttac tagcgttact ctgttccata       60
ccaataacgg cgtcaggtat atggctagct tcaaagccag acaacgagtg tgtcaatctc      120
ctccgttggc ccgttgtcgt cctcggcgtt tcatcctcg tcgtctccgc cacaggcttc      180
atcggcgcct acaagtacaa ggaaactcta ctggcgtttt acttgtgctg tatggcgata      240
ttgatcggac ttttgctggt ggttcttata tttgcattcg tcgtgacccg gcccgatgga      300
tcgtatcggg ttccgggtag aggttataaa gagtataggc ttgaagggtt ctcgaattgg      360
cttaaggaga acgttgtgga ttccaagaac tggggaaggc taagggcttg tttggctgat      420

```
actaatgttt gtcctaaact caaccaagaa ttcatcaccg ccgatcagtt cttctcctcc      480
tctaagatca ctcctctcca gtccggctgc tgcaaaccac caaccgcatg tggctacaac      540
tttgtgaacc caacactgtg gctaaatcca accaatatgg ctgcagacgc agactgttac      600
ttatggagca atgaccaaag ccagctttgt tacaattgca actcatgcaa agctggttta      660
ttgggaaacc ttagaaaaga atggcgtaaa gcaaatctca tacttatcat cacagtcgtt      720
gttctcatat gggtttatgt tattgcttgt agcgcgttta ggaatgctca gactgaggat      780
ctcttccgca aatacaaaca aggttgggtc taa                                   813
```

<210> SEQ ID NO 17
<211> LENGTH: 270
<212> TYPE: PRT
<213> ORGANISM: Arabidopsis thaliana

<400> SEQUENCE: 17

```
Met Ala Leu Ala Asn Asn Leu Thr Ala Ile Leu Asn Leu Leu Ala Leu
  1               5                  10                  15

Leu Cys Ser Ile Pro Ile Thr Ala Ser Gly Ile Trp Leu Ala Ser Lys
                 20                  25                  30

Pro Asp Asn Glu Cys Val Asn Leu Leu Arg Trp Pro Val Val Val Leu
             35                  40                  45

Gly Val Leu Ile Leu Val Val Ser Ala Thr Gly Phe Ile Gly Ala Tyr
         50                  55                  60

Lys Tyr Lys Glu Thr Leu Leu Ala Val Tyr Leu Cys Cys Met Ala Ile
 65                  70                  75                  80

Leu Ile Gly Leu Leu Leu Val Val Leu Ile Phe Ala Phe Val Val Thr
                 85                  90                  95

Arg Pro Asp Gly Ser Tyr Arg Val Pro Gly Arg Gly Tyr Lys Glu Tyr
            100                 105                 110

Arg Leu Glu Gly Phe Ser Asn Trp Leu Lys Glu Asn Val Val Asp Ser
        115                 120                 125

Lys Asn Trp Gly Arg Leu Arg Ala Cys Leu Ala Asp Thr Asn Val Cys
    130                 135                 140

Pro Lys Leu Asn Gln Glu Phe Ile Thr Ala Asp Gln Phe Phe Ser Ser
145                 150                 155                 160

Ser Lys Ile Thr Pro Leu Gln Ser Gly Cys Cys Lys Pro Pro Thr Ala
                165                 170                 175

Cys Gly Tyr Asn Phe Val Asn Pro Thr Leu Trp Leu Asn Pro Thr Asn
            180                 185                 190

Met Ala Ala Asp Ala Asp Cys Tyr Leu Trp Ser Asn Asp Gln Ser Gln
        195                 200                 205

Leu Cys Tyr Asn Cys Asn Ser Cys Lys Ala Gly Leu Leu Gly Asn Leu
    210                 215                 220

Arg Lys Glu Trp Arg Lys Ala Asn Leu Ile Leu Ile Ile Thr Val Val
225                 230                 235                 240

Val Leu Ile Trp Val Tyr Val Ile Ala Cys Ser Ala Phe Arg Asn Ala
                245                 250                 255

Gln Thr Glu Asp Leu Phe Arg Lys Tyr Lys Gln Gly Trp Val
            260                 265                 270
```

<210> SEQ ID NO 18
<211> LENGTH: 816
<212> TYPE: DNA
<213> ORGANISM: Arabidopsis thaliana

```
<400> SEQUENCE: 18
atgtttcgag ttagcaattt catggttggt ctagcaaaca cattggtgat gttagtgggc    60
gcttcggcca ttggttattc gatttacatg ttcgttcacc aaggcgtcac tgattgtgaa   120
tctgccattc ggataccact ctcacgacc ggactcatcc tcttcttggt gtctttgctc    180
ggagtgattg gatcttgttt caaggagaat ttggcaatgg tttcctactt gatcatattg   240
tttgggggca ttgttgcatt gatgattttc tccatatttc tcttctttgt gaccaacaaa   300
ggagccggtc gtgtggtgtc cggtcgaggg tataaagagt accggacggt ggatttctcg   360
acgtggctta atgggttcgt tggtgggaag agatgggttg gataaggtc ttgtttggct    420 gaggctaacg tttgtgatga tttgagtgat ggtcgtgtta gtcagatcgc tgatgcgttt   480
tatcacaaga acttgtctcc catccagtca ggttgttgta agccaccatc ggattgcaac   540
ttcgagttca gaaacgcgac gttctggata ccgccagca aaaacgaaac ggcagttgcg    600
gaaacggggg actgtggtac gtggagcaac gtgcaaacag agttatgttt caactgcaac   660
gcatgcaaag cgggtgtgtt agcgaacata agagagaagt ggaggaatct tcttgttttc   720
aacatttgtc tcctcattct cctcataacc gtctattcct gcggttgctg tgctcgtcgt   780
aacaatcgga cggctaggaa aagtgattct gtctga                             816

<210> SEQ ID NO 19
<211> LENGTH: 271
<212> TYPE: PRT
<213> ORGANISM: Arabidopsis thaliana

<400> SEQUENCE: 19

Met Phe Arg Val Ser Asn Phe Met Val Gly Leu Ala Asn Thr Leu Val
  1               5                  10                  15

Met Leu Val Gly Ala Ser Ala Ile Gly Tyr Ser Ile Tyr Met Phe Val
                 20                  25                  30

His Gln Gly Val Thr Asp Cys Glu Ser Ala Ile Arg Ile Pro Leu Leu
             35                  40                  45

Thr Thr Gly Leu Ile Leu Phe Leu Val Ser Leu Gly Val Ile Gly
         50                  55                  60

Ser Cys Phe Lys Glu Asn Leu Ala Met Val Ser Tyr Leu Ile Ile Leu
 65                  70                  75                  80

Phe Gly Gly Ile Val Ala Leu Met Ile Phe Ser Ile Phe Leu Phe Phe
                 85                  90                  95

Val Thr Asn Lys Gly Ala Gly Arg Val Val Ser Gly Arg Gly Tyr Lys
            100                 105                 110

Glu Tyr Arg Thr Val Asp Phe Ser Thr Trp Leu Asn Gly Phe Val Gly
        115                 120                 125

Gly Lys Arg Trp Val Gly Ile Arg Ser Cys Leu Ala Glu Ala Asn Val
    130                 135                 140

Cys Asp Asp Leu Ser Asp Gly Arg Val Ser Gln Ile Ala Asp Ala Phe
145                 150                 155                 160

Tyr His Lys Asn Leu Ser Pro Ile Gln Ser Gly Cys Cys Lys Pro Pro
                165                 170                 175

Ser Asp Cys Asn Phe Glu Phe Arg Asn Ala Thr Phe Trp Ile Pro Pro
            180                 185                 190

Ser Lys Asn Glu Thr Ala Val Ala Glu Asn Gly Asp Cys Gly Thr Trp
        195                 200                 205

Ser Asn Val Gln Thr Glu Leu Cys Phe Asn Cys Asn Ala Cys Lys Ala
    210                 215                 220
```

```
Gly Val Leu Ala Asn Ile Arg Glu Lys Trp Arg Asn Leu Leu Val Phe
225                 230                 235                 240

Asn Ile Cys Leu Leu Ile Leu Ile Thr Val Tyr Ser Cys Gly Cys
                245                 250                 255

Cys Ala Arg Arg Asn Asn Arg Thr Ala Arg Lys Ser Asp Ser Val
            260                 265                 270

<210> SEQ ID NO 20
<211> LENGTH: 705
<212> TYPE: DNA
<213> ORGANISM: Arabidopsis thaliana

<400> SEQUENCE: 20
atgagcaata cagtgatagg attcttgaat atcctaacac taatttcctc catagttcta     60
ttaggatcag ctctatggat gggtaggagc aaaacgacat gcgagcattt tcttcagaag    120
ccacttttga tcttaggcct agctatcttg atcttgtcag tagctggtct agtcggtgca    180
tgttgtgacg tggcttgggt cttgtgggtg tacctcttct tcatggtctt catcatagtc    240
gcactcatgg gtttgacctt gtttggattc atagtgacta ccatagtgg tggtgtggtt    300 gtcgatggta gggtttataa agagtttaag cttgaagcat atcacccttg gcttaagaca    360
agggtggtag atactaatta tgggttact ataaagactt gtctcttggg ctcagtcact    420
tgttccaagc tcgctctttg gactcctctt gattatctcc aaaaagactt atctcctctt    480
cagctgttta ctgtgttggc tgttgcgcgt ttaaaaacgc caaacgccct caacattacg    540 gcttcccta tggacgttac ggcatgtcca atccagacc tggatgggaa cagtcctggt    600
ttgttctctt ttctaatgca acaattattt ttattatttt cgcggcatgt aggtcaaggt    660
ggtggcatgg gagagatcgg tattagtgaa aaatatttat gttaa                   705

<210> SEQ ID NO 21
<211> LENGTH: 234
<212> TYPE: PRT
<213> ORGANISM: Arabidopsis thaliana

<400> SEQUENCE: 21

Met Ser Asn Thr Val Ile Gly Phe Leu Asn Ile Leu Thr Leu Ile Ser
1               5                   10                  15

Ser Ile Val Leu Leu Gly Ser Ala Leu Trp Met Gly Arg Ser Lys Thr
                20                  25                  30

Thr Cys Glu His Phe Leu Gln Lys Pro Leu Leu Ile Leu Gly Leu Ala
            35                  40                  45

Ile Leu Ile Leu Ser Val Ala Gly Leu Val Gly Ala Cys Cys Asp Val
        50                  55                  60

Ala Trp Val Leu Trp Val Tyr Leu Phe Phe Met Val Phe Ile Ile Val
65                  70                  75                  80

Ala Leu Met Gly Leu Thr Leu Phe Gly Phe Ile Val Thr Ser His Ser
                85                  90                  95

Gly Gly Val Val Val Asp Gly Arg Val Tyr Lys Glu Phe Lys Leu Glu
                100                 105                 110

Ala Tyr His Pro Trp Leu Lys Thr Arg Val Val Asp Thr Asn Tyr Trp
            115                 120                 125

Val Thr Ile Lys Thr Cys Leu Leu Gly Ser Val Thr Cys Ser Lys Leu
        130                 135                 140

Ala Leu Trp Thr Pro Leu Asp Tyr Leu Gln Lys Asp Leu Ser Pro Leu
145                 150                 155                 160
```

```
Gln Leu Phe Thr Val Leu Ala Val Ala Arg Leu Lys Thr Pro Asn Ala
                165                 170                 175
Leu Asn Ile Thr Ala Ser Leu Met Asp Val Thr Ala Cys Pro Asn Pro
            180                 185                 190
Asp Leu Asp Gly Asn Ser Pro Gly Leu Phe Ser Phe Leu Met Gln Gln
        195                 200                 205
Leu Phe Leu Leu Phe Ser Arg His Val Gly Gln Gly Gly Met Gly
    210                 215                 220
Glu Ile Gly Ile Ser Glu Lys Tyr Leu Cys
225                 230
```

<210> SEQ ID NO 22
<211> LENGTH: 795
<212> TYPE: DNA
<213> ORGANISM: Arabidopsis thaliana

<400> SEQUENCE: 22

```
atgctccggc taagcaacgc cgccgtaata caaccaatg caattctcgc attgatcggc        60
ctcgccgctc tatcttttc cgtctacgtc tacgttcaag cccatcaca gtgtcaacgt       120
ttcgttcaaa accctctcat tgtaactgcg gctctcctct tcttcatctc gtccttaggc       180
cttatcgctg ctctctacgg tagccacatc atcatcacac tctatctctt cttcctttc       240
ctctccattc ttctgcttct tgtcctctct gtctttatct tcctcgtcac gaatcccacc       300
gccggaaaag cgttatccgg tagaggaata ggcaatgtca agaccggaga ttatcagaac       360
tggatcggga accatttcct tcgtgggaag aattgggaag ggatcaccaa atgtttgtct       420
gattctaggg tttgtaaaag gtttggtcca cgtgacattg actttgactc caaacatctc       480
tctaatgtac agtttggttg ttgtcgacct cccgtagaat gtgggttcga atcaaagaat       540
gccacgtggt ggacagttcc tgccacagcg actacggcga ttataggga ttgtaaggca       600
tggagtaaca cgcagagaca gttatgttac gcgtgcgagt cgtgtaagat ggagttttta       660
aaagggataa gaaaaagatg gaggatactt attgtcgtca atctccttct tatccttctc       720
gtcgtttttc tttactcgtg tggctgttgc gtgagaaaga acaatcgtgt tccatggaag       780
cgccggttct tctaa                                                        795
```

<210> SEQ ID NO 23
<211> LENGTH: 264
<212> TYPE: PRT
<213> ORGANISM: Arabidopsis thaliana

<400> SEQUENCE: 23

```
Met Leu Arg Leu Ser Asn Ala Ala Val Ile Thr Thr Asn Ala Ile Leu
  1               5                  10                  15
Ala Leu Ile Gly Leu Ala Ala Leu Ser Phe Ser Val Tyr Val Tyr Val
             20                  25                  30
Gln Gly Pro Ser Gln Cys Gln Arg Phe Val Gln Asn Pro Leu Ile Val
         35                  40                  45
Thr Ala Ala Leu Leu Phe Phe Ile Ser Ser Leu Gly Leu Ile Ala Ala
     50                  55                  60
Leu Tyr Gly Ser His Ile Ile Ile Thr Leu Tyr Leu Phe Phe Leu Phe
 65                  70                  75                  80
Leu Ser Ile Leu Leu Leu Val Leu Ser Val Phe Ile Phe Leu Val
                 85                  90                  95
Thr Asn Pro Thr Ala Gly Lys Ala Leu Ser Gly Arg Gly Ile Gly Asn
            100                 105                 110
```

```
Val Lys Thr Gly Asp Tyr Gln Asn Trp Ile Gly Asn His Phe Leu Arg
        115                 120                 125

Gly Lys Asn Trp Glu Gly Ile Thr Lys Cys Leu Ser Asp Ser Arg Val
130                 135                 140

Cys Lys Arg Phe Gly Pro Arg Asp Ile Asp Phe Asp Ser Lys His Leu
145                 150                 155                 160

Ser Asn Val Gln Phe Gly Cys Cys Arg Pro Val Glu Cys Gly Phe
            165                 170                 175

Glu Ser Lys Asn Ala Thr Trp Trp Thr Val Pro Ala Thr Ala Thr Thr
            180                 185                 190

Ala Ile Ile Gly Asp Cys Lys Ala Trp Ser Asn Thr Gln Arg Gln Leu
        195                 200                 205

Cys Tyr Ala Cys Glu Ser Cys Lys Ile Gly Val Leu Lys Gly Ile Arg
        210                 215                 220

Lys Arg Trp Arg Ile Leu Ile Val Val Asn Leu Leu Ile Leu Leu
225                 230                 235                 240

Val Val Phe Leu Tyr Ser Cys Gly Cys Cys Val Arg Lys Asn Asn Arg
            245                 250                 255

Val Pro Trp Lys Arg Arg Phe Phe
            260
```

<210> SEQ ID NO 24
<211> LENGTH: 654
<212> TYPE: DNA
<213> ORGANISM: Arabidopsis thaliana

<400> SEQUENCE: 24

```
atgattgatt ttcctttgaa gtatcttgcc gtgctcctga tcgttttgat cgcgattctt      60
gtctttaccg tactggcgtt cattgtaaca acaatggttc tggccatac taaccctggt      120
ttaaggtaca aggagtataa gctgaatgat tacagctcat ggtttctaaa acagcttaac     180
aacaccagta actggataag actaaagagt tgtcttgtta atccgagca atgtcggaag      240
ctttccaaga aatacaagac catcaaacag ttgaaatccg cagaattaac ccgatagaa     300
gctggatgtt gtcgaccacc atctgagtgt ggttatcctg cggtgaatgc ttcttactat   360
gacttgagct tcattcgat aagttctaac aaagattgta agcttacaa gaatttgagg      420
actatcaagt gctacaactg tgattcttgc aaagctggag ttgctcagta catgaaaacc    480
gagtggcgac ttgttgcgat cttcaatgtg gtcctgtttg ttgtcttgat aagctctctt    540
cttagcacga gatttgactc tgaacaaagt tttggccttt taaacggttt agtgcaaatt    600
tccaacataa ccttttaaaga ttgccaaacc acaacagtac caaaacagtt ttaa        654
```

<210> SEQ ID NO 25
<211> LENGTH: 217
<212> TYPE: PRT
<213> ORGANISM: Arabidopsis thaliana

<400> SEQUENCE: 25

```
Met Ile Asp Phe Pro Leu Lys Tyr Leu Ala Val Leu Leu Ile Val Leu
1               5                   10                  15

Ile Ala Ile Leu Val Phe Thr Val Leu Ala Phe Ile Val Thr Asn Asn
            20                  25                  30

Gly Ser Gly His Thr Asn Pro Gly Leu Arg Tyr Lys Glu Tyr Lys Leu
        35                  40                  45

Asn Asp Tyr Ser Ser Trp Phe Leu Lys Gln Leu Asn Asn Thr Ser Asn
50                  55                  60
```

```
Trp Ile Arg Leu Lys Ser Cys Leu Val Lys Ser Glu Gln Cys Arg Lys
 65                  70                  75                  80

Leu Ser Lys Lys Tyr Lys Thr Ile Lys Gln Leu Lys Ser Ala Glu Leu
                 85                  90                  95

Thr Pro Ile Glu Ala Gly Cys Cys Arg Pro Pro Ser Glu Cys Gly Tyr
            100                 105                 110

Pro Ala Val Asn Ala Ser Tyr Tyr Asp Leu Ser Phe His Ser Ile Ser
        115                 120                 125

Ser Asn Lys Asp Cys Lys Leu Tyr Lys Asn Leu Arg Thr Ile Lys Cys
    130                 135                 140

Tyr Asn Cys Asp Ser Cys Lys Ala Gly Val Ala Gln Tyr Met Lys Thr
145                 150                 155                 160

Glu Trp Arg Leu Val Ala Ile Phe Asn Val Val Leu Phe Val Val Leu
                165                 170                 175

Ile Ser Ser Leu Leu Ser Thr Arg Phe Asp Ser Glu Gln Ser Phe Gly
            180                 185                 190

Leu Leu Asn Gly Leu Val Gln Ile Ser Asn Ile Thr Phe Lys Asp Cys
        195                 200                 205

Gln Thr Thr Thr Val Pro Lys Gln Phe
    210                 215
```

<210> SEQ ID NO 26
<211> LENGTH: 837
<212> TYPE: DNA
<213> ORGANISM: Arabidopsis thaliana

<400> SEQUENCE: 26

```
atggcgagag ataaagaaga tcaaaacaat gagaatcctt caattgtcca gaacatgtca      60
tttccattca acaccatttt cttgatctca agcgcaatct tcctcgtcac agccgctttc     120
tggttcgtag ccgtcatgac attacattac aggaccgatg aatgtaaccg gttcgtcaca     180
actcccggaa tattcataag cttctcattg cttgctatgt ccctcactgg attctacgca     240
gcttacttca aatccgattg tctctttcga atccacttct ttatcttctt cttgtggatg     300
ttcgttgtcg tgtctaaagc aatctttgtc atctttctac ataaggagac caatcctaga     360
ttgtttcctg ggaccaagat ttatgagttt aggtacgagg attactcagg atgggttagt     420
agattggtca tcaaagacga tgaatggtat cgtacaagga gatgtcttgt taaggacaat     480
gtttgtaaca ggctaaaacca taagatgcca gcttctgagt tttatcagat gaatctaact     540
cctatacagt cgggttgttg caaaccacca ctttcatgtg gattgaatta cgagaaacca     600
aataattgga cagtttcaag atattataac aatttagaag ttgattgcaa gagatggaac     660
aattctgcag atacattatg cttcgattgt gattcatgta aagctgtgat tattgctgat     720
gtacataata cttcattttc cataacagtt aacattattc atatcatctt tagtctttgt     780
atcggcatga ccggttggtt tgcctggtta aggatccttc gagaaagtca gaaatag        837
```

<210> SEQ ID NO 27
<211> LENGTH: 278
<212> TYPE: PRT
<213> ORGANISM: Arabidopsis thaliana

<400> SEQUENCE: 27

```
Met Ala Arg Asp Lys Glu Asp Gln Asn Asn Glu Asn Pro Ser Ile Val
 1               5                  10                  15

Gln Asn Met Ser Phe Pro Phe Asn Thr Ile Phe Leu Ile Ser Ser Ala
             20                  25                  30
```

```
Ile Phe Leu Val Thr Ala Ala Phe Trp Phe Val Ala Val Met Thr Leu
        35                  40                  45

His Tyr Arg Thr Asp Glu Cys Asn Arg Phe Val Thr Thr Pro Gly Ile
    50                  55                  60

Phe Ile Ser Phe Ser Leu Leu Ala Met Ser Leu Thr Gly Phe Tyr Ala
65                  70                  75                  80

Ala Tyr Phe Lys Ser Asp Cys Leu Phe Arg Ile His Phe Phe Ile Phe
                85                  90                  95

Phe Leu Trp Met Phe Val Val Ser Lys Ala Ile Phe Val Ile Phe
            100                 105                 110

Leu His Lys Glu Thr Asn Pro Arg Leu Phe Pro Gly Thr Lys Ile Tyr
        115                 120                 125

Glu Phe Arg Tyr Glu Asp Tyr Ser Gly Trp Val Ser Arg Leu Val Ile
    130                 135                 140

Lys Asp Asp Glu Trp Tyr Arg Thr Arg Arg Cys Leu Val Lys Asp Asn
145                 150                 155                 160

Val Cys Asn Arg Leu Asn His Lys Met Pro Ala Ser Glu Phe Tyr Gln
                165                 170                 175

Met Asn Leu Thr Pro Ile Gln Ser Gly Cys Cys Lys Pro Pro Leu Ser
            180                 185                 190

Cys Gly Leu Asn Tyr Glu Lys Pro Asn Asn Trp Thr Val Ser Arg Tyr
        195                 200                 205

Tyr Asn Asn Leu Glu Val Asp Cys Lys Arg Trp Asn Asn Ser Ala Asp
    210                 215                 220

Thr Leu Cys Phe Asp Cys Asp Ser Cys Lys Ala Val Ile Ile Ala Asp
225                 230                 235                 240

Val His Asn Thr Ser Phe Ser Ile Thr Val Asn Ile Ile His Ile Ile
                245                 250                 255

Phe Ser Leu Cys Ile Gly Met Thr Gly Trp Phe Ala Trp Leu Arg Ile
            260                 265                 270

Leu Arg Glu Ser Gln Lys
        275

<210> SEQ ID NO 28
<211> LENGTH: 816
<212> TYPE: DNA
<213> ORGANISM: Arabidopsis thaliana

<400> SEQUENCE: 28
atgggaacat tgatggcact tgtgaacatt ttagccgctg gtgtccttcc gatcttcact      60
ttcgtcctct cacttacact cctcggctac gcagtgtggc ttctttacat gcgtagctac     120
gactgcgaag atattctcgg tctgccacgt gtccagacgc tagctagtgt cggtcttctc     180
gcggtgtttg ttgtcagcaa cgcagctctg tttttgcggc ggaagtttcc gatgcctgca     240
cttgtggtga tggtggtggt cttgttgtta atgcttttca tcggtttggc gtatgccgga     300
gtaaatgaga tgcaaagccg gcggtttccg gcgacaagga tgtggttcaa gctcaaaatc     360
atggacgatc atgtgacctg aacaatatc aaatcgtgtg tctatgataa aggagcttgc     420
aacgacctca tttacggatc tccaaatgaa aaaccttaca atagaagaaa aatgccacca     480
atcaagaatg gatgttgtat gccaccagag acatgtaaca tggacgcgat aaacgcgacg     540 tttggtaca agagaaaaga cgaaggacca ccgtcgtcta tgaacctaat gtacggtgat     600
gagatgatgg tgggaaggat tagcgactgt caactatgga ggaacgattg gagcatttta     660
tgctatgatt gtagatcttg taagttcgga ttcataagat cggtaaggag gaaatggtgg     720
```

```
cagctcggta tcttcttgat cgtcatttcc attcttcttc tcatgtctca tctcttgatc    780
ttcttggcta cttttggga acgattcaag ggttag                              816
```

<210> SEQ ID NO 29
<211> LENGTH: 271
<212> TYPE: PRT
<213> ORGANISM: Arabidopsis thaliana

<400> SEQUENCE: 29

```
Met Gly Thr Leu Met Ala Leu Val Asn Ile Leu Ala Ala Gly Val Leu
 1               5                  10                  15

Pro Ile Phe Thr Phe Val Leu Ser Leu Thr Leu Leu Gly Tyr Ala Val
            20                  25                  30

Trp Leu Leu Tyr Met Arg Ser Tyr Asp Cys Glu Asp Ile Leu Gly Leu
        35                  40                  45

Pro Arg Val Gln Thr Leu Ala Ser Val Gly Leu Leu Ala Val Phe Val
    50                  55                  60

Val Ser Asn Ala Ala Leu Phe Leu Arg Arg Lys Phe Pro Met Pro Ala
65                  70                  75                  80

Leu Val Val Met Val Val Leu Leu Leu Met Leu Phe Ile Gly Leu
                85                  90                  95

Ala Tyr Ala Gly Val Asn Glu Met Gln Ser Arg Arg Phe Pro Ala Thr
            100                 105                 110

Arg Met Trp Phe Lys Leu Lys Ile Met Asp Asp His Val Thr Trp Asn
        115                 120                 125

Asn Ile Lys Ser Cys Val Tyr Asp Lys Gly Ala Cys Asn Asp Leu Ile
    130                 135                 140

Tyr Gly Ser Pro Asn Glu Lys Pro Tyr Asn Arg Arg Lys Met Pro Pro
145                 150                 155                 160

Ile Lys Asn Gly Cys Cys Met Pro Pro Glu Thr Cys Asn Met Asp Ala
                165                 170                 175

Ile Asn Ala Thr Phe Trp Tyr Arg Arg Lys Asp Glu Gly Pro Pro Ser
            180                 185                 190

Ser Met Asn Leu Met Tyr Gly Asp Glu Met Met Val Gly Arg Ile Ser
        195                 200                 205

Asp Cys Gln Leu Trp Arg Asn Asp Trp Ser Ile Leu Cys Tyr Asp Cys
    210                 215                 220

Arg Ser Cys Lys Phe Gly Phe Ile Arg Ser Val Arg Arg Lys Trp Trp
225                 230                 235                 240

Gln Leu Gly Ile Phe Leu Ile Val Ile Ser Ile Leu Leu Leu Met Ser
                245                 250                 255

His Leu Leu Ile Phe Leu Ala Thr Phe Trp Glu Arg Phe Lys Gly
            260                 265                 270
```

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence:vector pSKI015

<400> SEQUENCE: 30

```
gcggcagcgg cggcaggata tatt                                          24
```

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 31
tgctttcgcc tataaatacg acgg                                          24

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 32
cgctgcggac atctacattt ttg                                           23

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 33
tcccggacat gaagccattt ac                                            22

<210> SEQ ID NO 34
<211> LENGTH: 16
<212> TYPE: DNA
<213> ORGANISM: Artificial Sequence
<220> FEATURE:
<221> NAME/KEY: modified_base
<222> LOCATION: 1 and 11
<223> OTHER INFORMATION: n represents a,g,c or t
<220> FEATURE:
<221> NAME/KEY: modified_base
<222> LOCATION: 7
<223> OTHER INFORMATION: s represents g or c
<220> FEATURE:
<221> NAME/KEY: modified_base
<222> LOCATION: 8 and 13
<223> OTHER INFORMATION: w represents a or t
<220> FEATURE:
<223> OTHER INFORMATION: Description of Artificial Sequence:primer

<400> SEQUENCE: 34
ngtcgaswga nawgaa                                                   16

<210> SEQ ID NO 35
<211> LENGTH: 278
<212> TYPE: DNA
<213> ORGANISM: Artificial Sequence
<220> FEATURE:
<221> NAME/KEY: modified_base
<222> LOCATION: 13, 35, 73, 108, 156, 190, 198 and 201
<223> OTHER INFORMATION: n represents a,g,c or t
<220> FEATURE:
<223> OTHER INFORMATION: Description of Artificial Sequence:PCR product
     from Arabidopsis thaliana

<400> SEQUENCE: 35
tgtggcaaac tcngagtagg aatggagaat ccaancgttt gggtctttct caaggaagaa    60
agtgacgact gcncattgta ttgctccgaa taaacacatc catgctgnta aagagaggtt   120
atctggatag taggcagaga ttggaaccta gggttntgtt gaaacaaaac tcacatttct   180

```
tgtaagacan gaaacatnca ncaacaaaaa gtttagactt ttgatttatt taatgaagtt        240
acctgaagta taagccaaaa ggaccaacaa agagtgct                                278
```

```
<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 36
cttcttcaat catcaccatg                                                    20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 37
tagcttgaac cggcgcaaat                                                    20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 38
gtacgtttta gtaacagtct                                                    20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 39
gattagcagt gactaactcc                                                    20

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 40
agcttgtaca ttaaccgtga ct                                                 22

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 41
ctgcagggtg atgattgaag aagat                                              25
```